(12) United States Patent
Muramatsu et al.

(10) Patent No.: US 7,520,882 B2
(45) Date of Patent: *Apr. 21, 2009

(54) APPARATUS FOR LIGATING LIVING TISSUES

(75) Inventors: Junichi Muramatsu, Akiruno (JP); Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/231,106

(22) Filed: Sep. 20, 2005

(65) Prior Publication Data
US 2006/0079911 A1 Apr. 13, 2006

Related U.S. Application Data

(62) Division of application No. 10/098,897, filed on Mar. 14, 2002, now Pat. No. 7,081,121.

(30) Foreign Application Priority Data
Mar. 14, 2001 (JP) ............................ 2001-072154

(51) Int. Cl.
*A61B 17/10* (2006.01)
*A61B 17/08* (2006.01)
(52) U.S. Cl. .................. 606/142; 606/139; 606/151
(58) Field of Classification Search ............ 606/75, 606/139, 142, 151, 219; 227/175.1
See application file for complete search history.

(56) References Cited

U.S. PATENT DOCUMENTS

| | | | | |
|---|---|---|---|---|
| 5,766,189 | A * | 6/1998 | Matsuno | 606/139 |
| 6,350,269 | B1 * | 2/2002 | Shipp et al. | 606/143 |
| 6,923,818 | B2 * | 8/2005 | Muramatsu et al. | 606/142 |
| 7,041,118 | B2 * | 5/2006 | Muramatsu et al. | 606/207 |
| 7,081,121 | B2 * | 7/2006 | Muramatsu et al. | 606/142 |

FOREIGN PATENT DOCUMENTS

| | | |
|---|---|---|
| DE | 102 09 843 A1 | 5/2003 |
| JP | 63-267345 | 11/1988 |
| JP | 2-6011 | 1/1990 |

\* cited by examiner

*Primary Examiner*—Julian W Woo
(74) *Attorney, Agent, or Firm*—Scully, Scott, Murphy & Presser, P.C.

(57) ABSTRACT

A apparatus for ligating living tissues comprises an introducing tube capable of being inserted into a living body cavity, at least two or more manipulating wires movably inserted into the introducing tube, and at least two or more clips having a proximal end portion, a pinch section being formed at a distal end of an arm section extending from the proximal end. This clipping apparatus is characterized in that a plurality of clips are arranged in series in the introducing tube so as to engage the clip and the manipulating wire with each other, respectively.

11 Claims, 17 Drawing Sheets

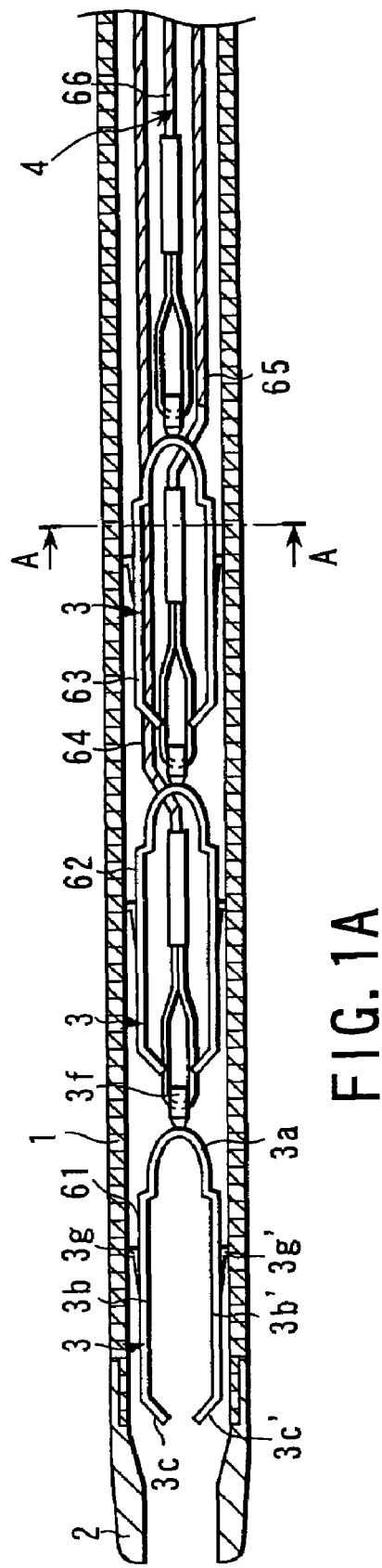
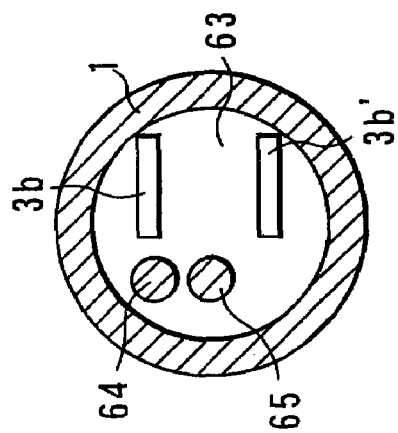
FIG. 1A
FIG. 1B

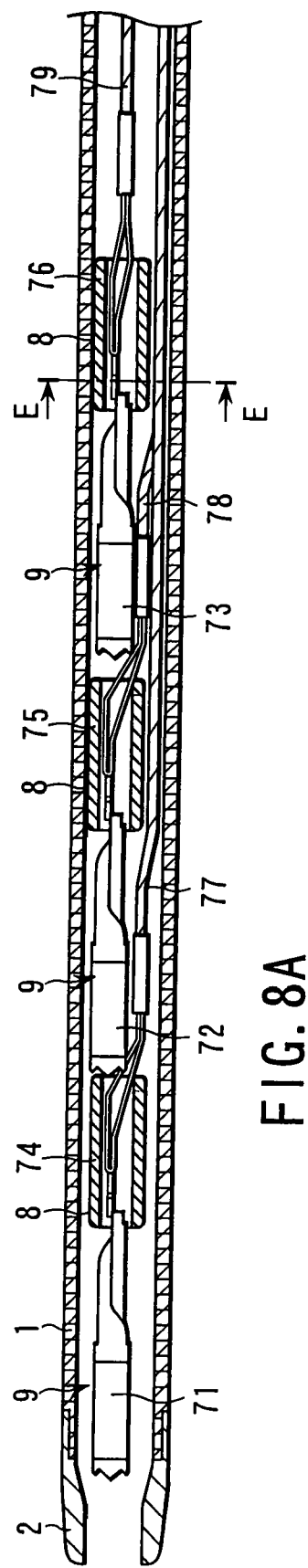
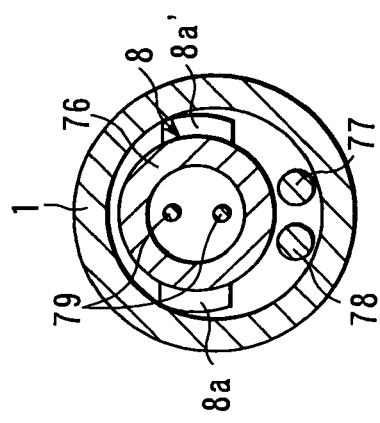
FIG. 8A
FIG. 8B

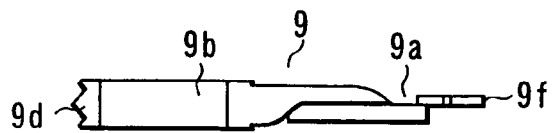
FIG. 10A
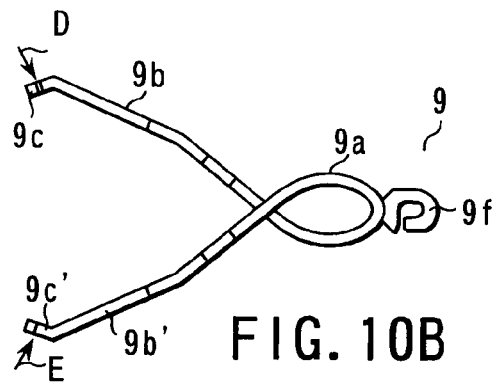
FIG. 10B
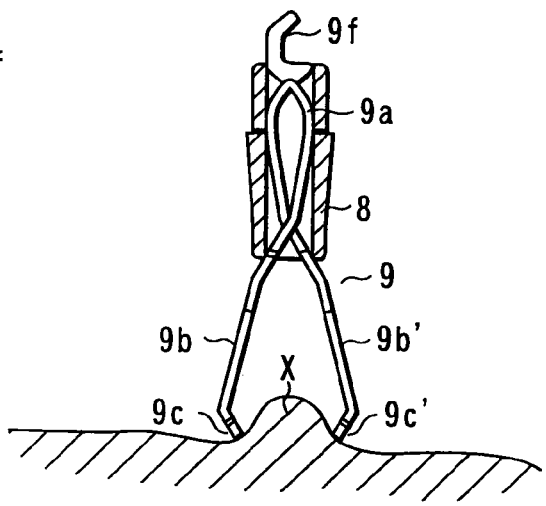
FIG. 13
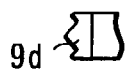 
FIG. 10C  FIG. 10D
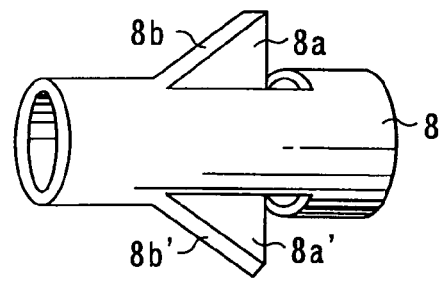
FIG. 11
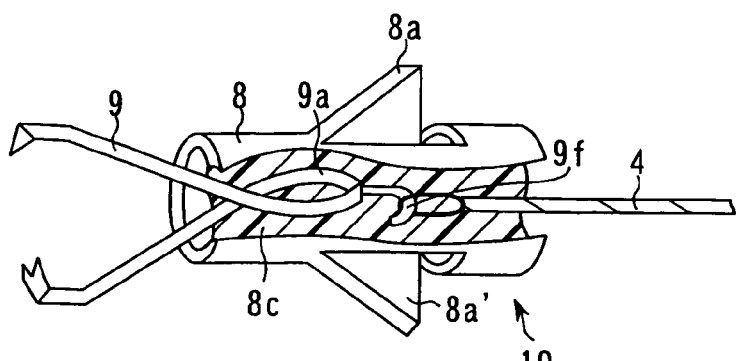
FIG. 12

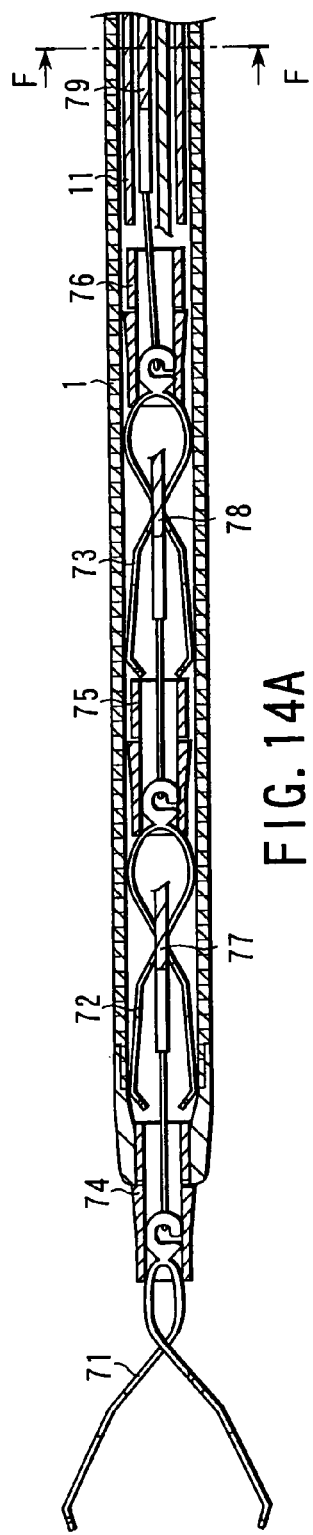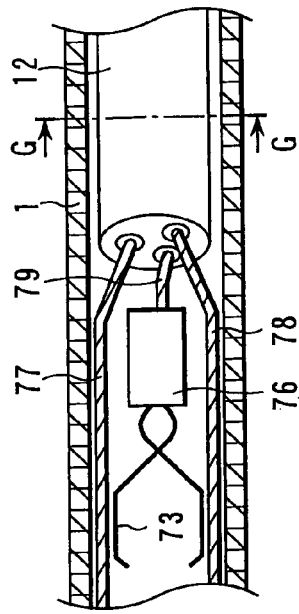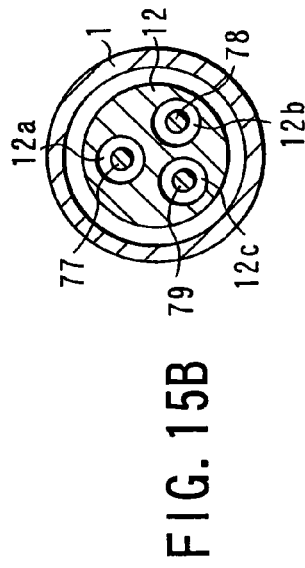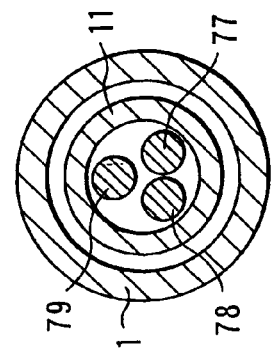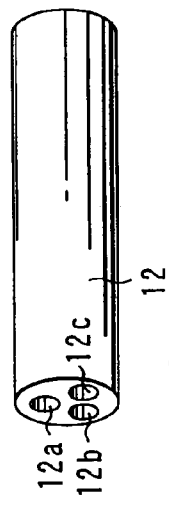
FIG. 14A
FIG. 14B
FIG. 15A
FIG. 15B
FIG. 16

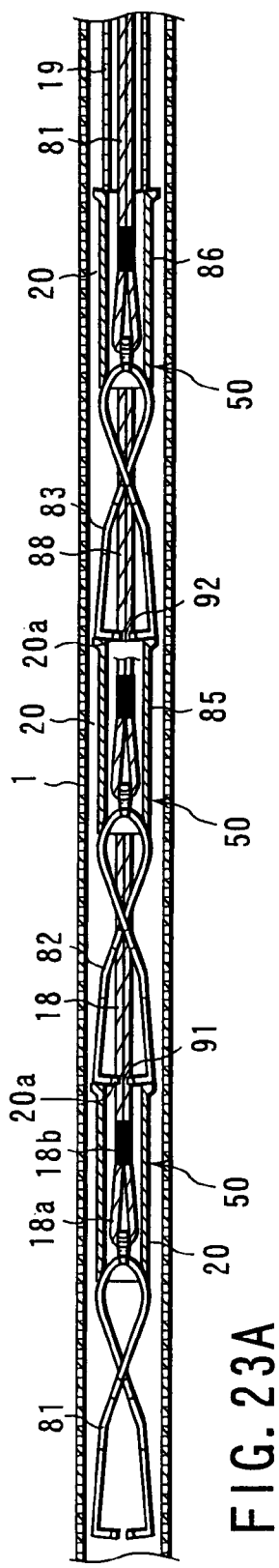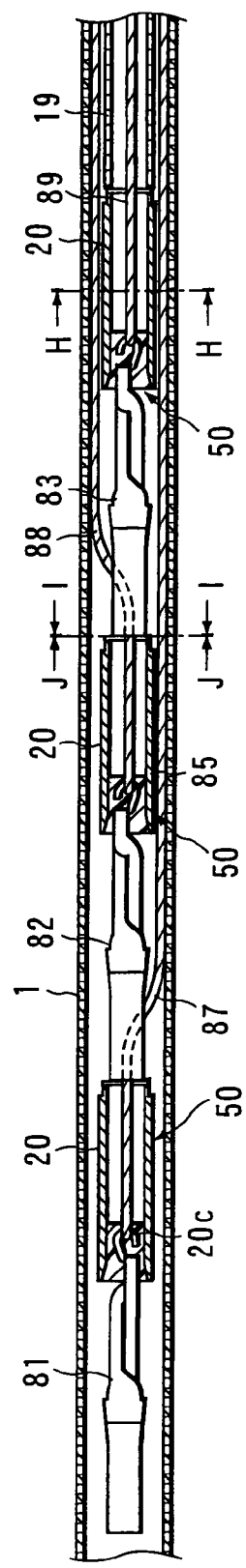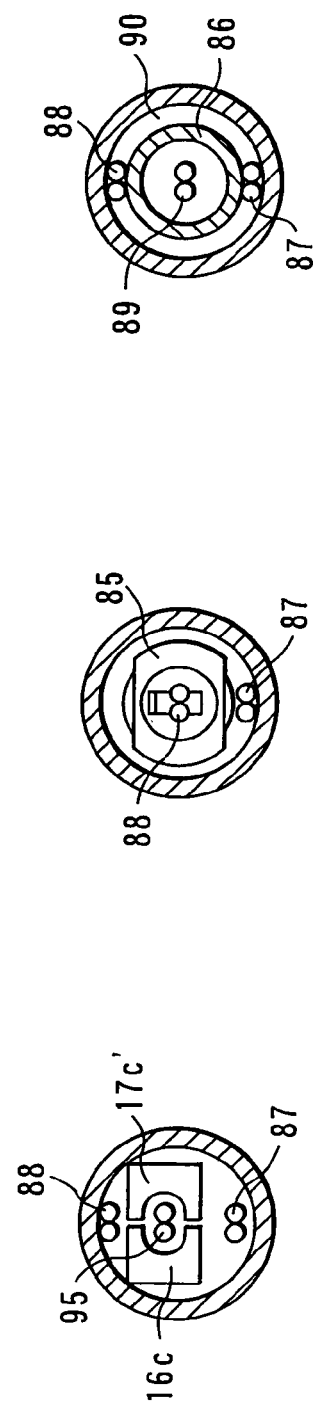

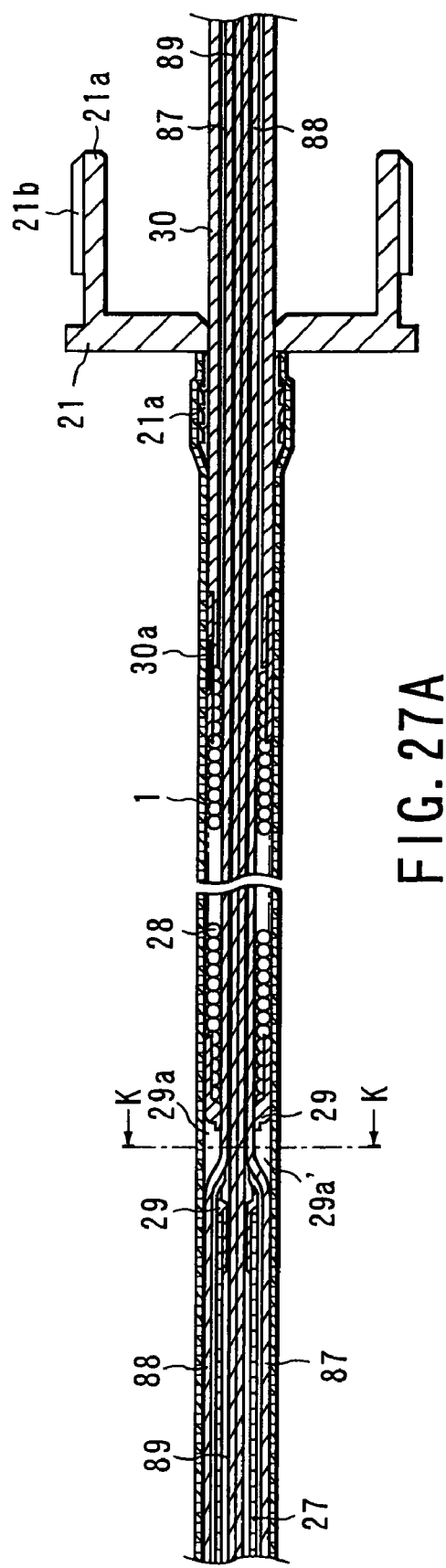
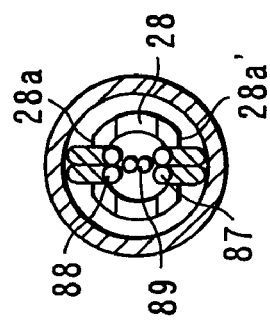
FIG. 27A
FIG. 27B

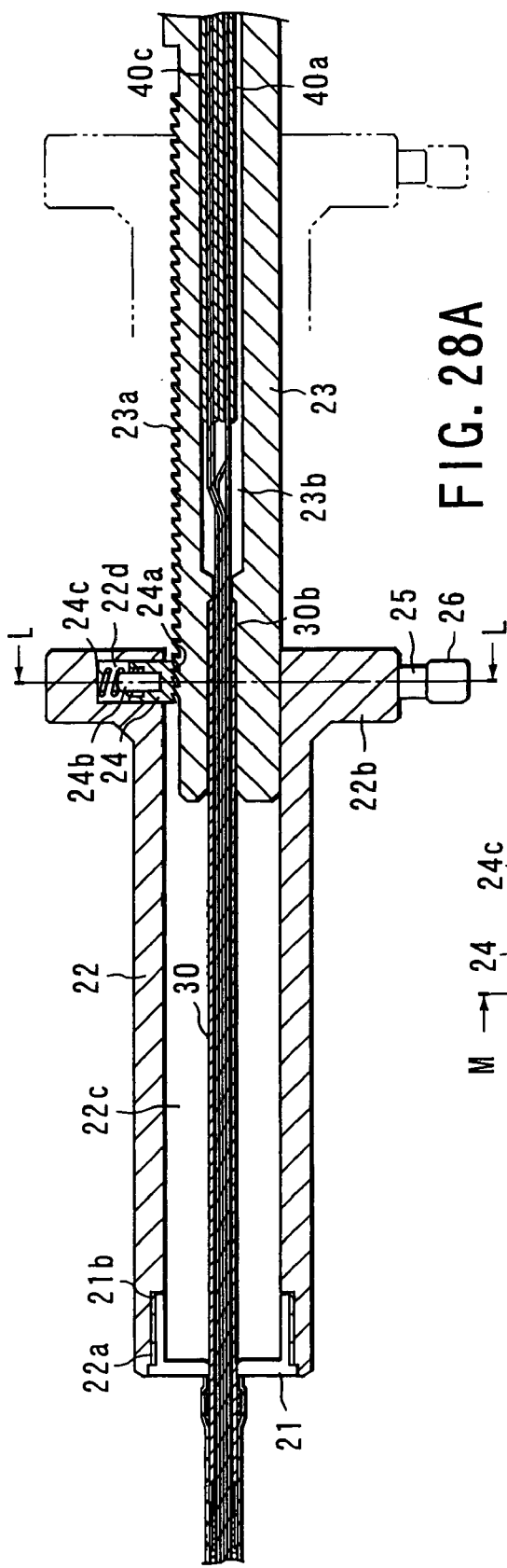
FIG. 28A
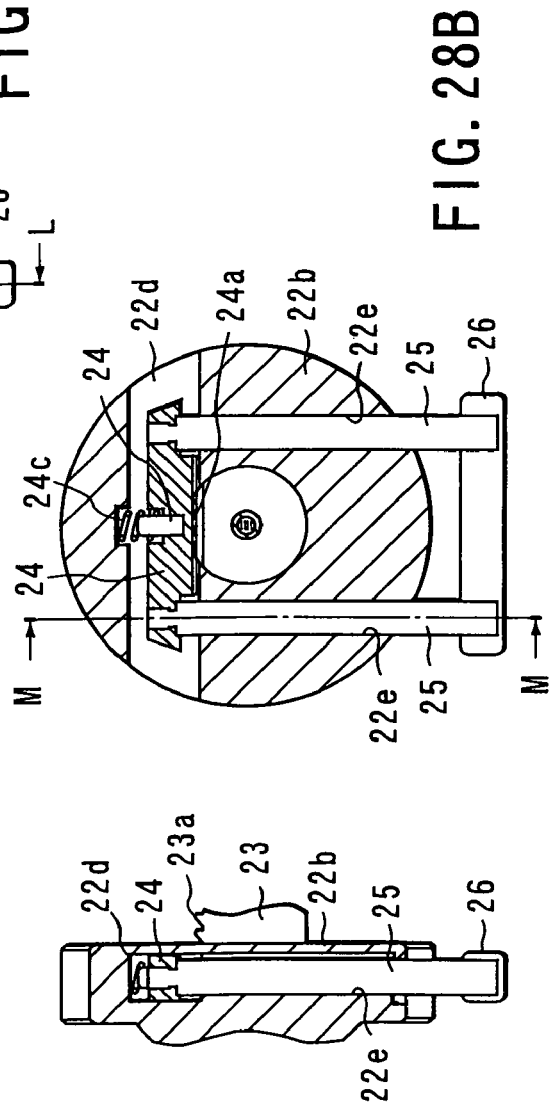
FIG. 28B
FIG. 28C

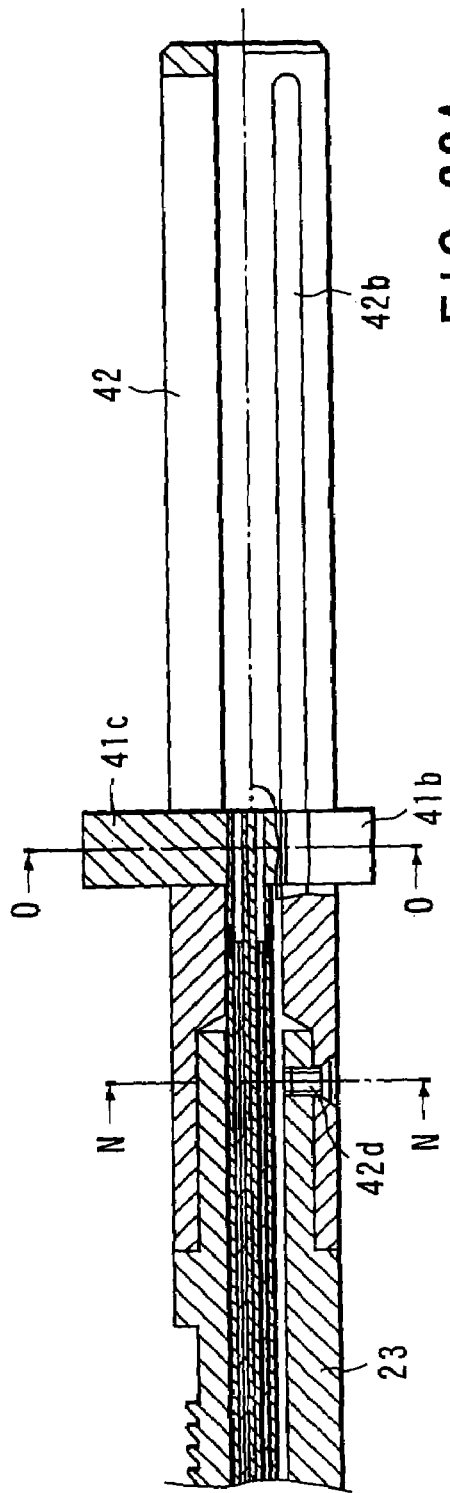
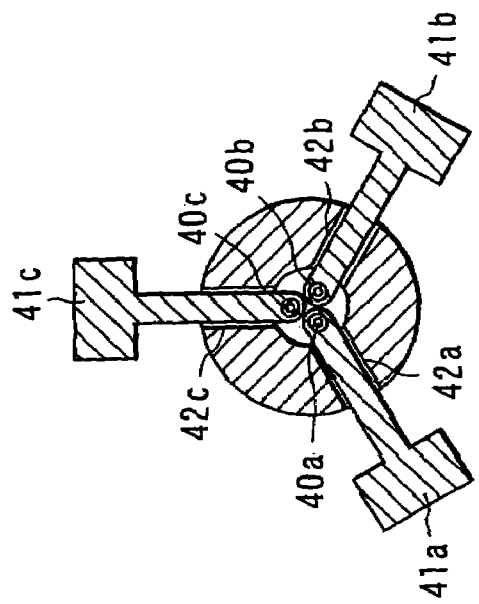
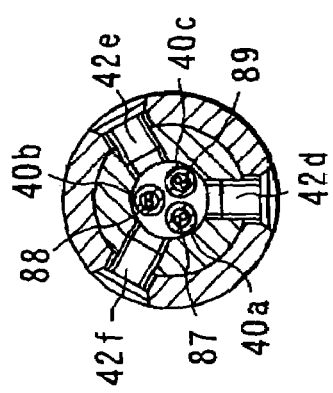
FIG. 29A
FIG. 29C
FIG. 29B

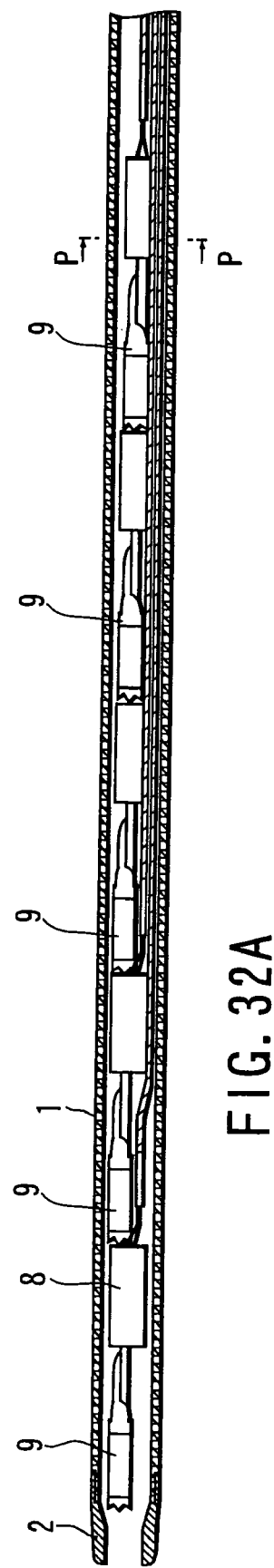
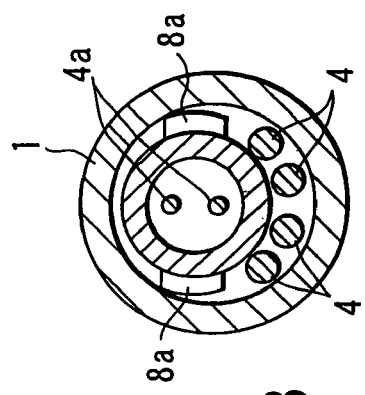
FIG. 32A
FIG. 32B

APPARATUS FOR LIGATING LIVING TISSUES

CROSS-REFERENCE TO RELATED APPLICATIONS

This application is a divisional of U.S. Ser. No. 10/098,897, filed Mar. 14, 2002, now U.S. Pat. No. 7,081,121 which is based upon and claims the benefit of priority from the prior Japanese Patent Application No. 2001-072154, filed Mar. 14, 2001, the entire contents of each of which are incorporated herein by reference.

BACKGROUND OF THE INVENTION

1. Field of the Invention

The present invention relates to a apparatus for ligating living tissues for inserting a living body cavity in a transendoscopic manner, thereby clipping a living tissue by a clip.

2. Description of the Related Art

Conventionally, it has been well known that a apparatus for ligating living tissues is disclosed in Jpn. UM. Appln. KOKAI Publication No. 2-6011 or Jpn. Pat. Appln. KOKAI Publication No. 63-267345, for example. In Jpn. UM. Appln. KOKAI Publication No. 2-6011, a clip and a manipulating wire are engaged with each other via a hook provided at a distal end portion of the manipulating wire and a connecting member provided at a tip end of the hook, the connecting member having a hook.

In addition, Jpn. Pat. Appln. KOKAI Publication No. 63-267345 discloses that a plurality of clips are incorporated in an introducing tube, these clips and a manipulating member are connected with each other with an aid of a substance with its low melting point, and the substance with its low melting point is fused while these clips and operating member are inserted into a body cavity so as to carry out clip ligation work continuously.

However, in the invention disclosed in Jpn. UM. Appln. KOKAI Publication No. 2-6011, only one clip can be mounted on a distal end of an introducing tube. Thus, only one clip can be used for each insertion into the body cavity through a forceps channel of an endoscope. Thus, in clipping a plurality of living tissues in a living body internal cavity, there has been a need to remove a clipping apparatus from the forceps channel of the endoscope every time, mount clips, and insert the mounted clips into the forceps channel again. Therefore, there has been a disadvantage that a complicated work is required, and too much time is required.

In addition, many cases of diseases such that a clip is applied to a bleeding site require very high emergency. Thus, in such cases of diseases, there has been a very serious problem that such a complicated, time consuming work is required.

In order to solve these problems, in Jpn. Pat. Appln. KOKAI Publication No. 63-267345, there is disclosed a clipping apparatus capable of carrying out ligation continuously by being inserted into a forceps channel only one time. In the thus-disclosed clipping apparatus, a plurality of clips are connected with each other by means of a substance with its low melting point. In addition, a temperature is controlled by a heating element provided at a tip end, thereby carrying out ligation continuously. That is, this structure is such that the heating element is heated up to a temperature at which the substance with its low melting point is fused, whereby these clips are disconnected from each other.

However, there has been a problem that providing a heating element at a distal end of a sheath complicates an apparatus structure, and requires another heat generating source. In addition, in order to open a clip made of a shape memory material, it is required to heat a clip up to a predetermined transform temperature T1. That is, after opening the clip, in order to fuse a substance with its melting point, and then, reliably ligate a living tissue, it is required to reliably control a relationship between a temperature T1 for opening a clip and a temperature T2 for fusing a substance with its low melting point. However, this temperature control has been very difficult. A clipping apparatus disclosed in Jpn. Pat. Appln. KOKAI Publication No. 63-267345 requires heating means for generating a heat during clip opening and during clip ligation. Thus, there has been a problem that clip ligation requires complicated work and much time.

BRIEF SUMMARY OF THE INVENTION

The present invention has been made in view of the foregoing circumstance. It is an object of the present invention to provide a apparatus for ligating living tissues with its high operability capable of carrying out clipping continuously while a plurality of clips are mounted on an introducing tube, and are inserted into a forceps channel one time.

According to the present invention, there can be provided a apparatus for ligating living tissues comprising:

an introducing tube capable of being inserted into a living body cavity;

at least two or more manipulating wires movably inserted into the introducing tube; and at least two or more clips each having a proximal end portion, the chips each forming a pinch section at a distal end of an arm section that extends from the proximal end portion, wherein the plurality of clips are arranged in series in the introducing tube, and the clips and the manipulating wire are engaged with each other.

In addition, according to the present invention, there can be provided a apparatus for ligating living tissues comprising:

an introducing tube capable of being inserted into a living body cavity;

a manipulating wire movably inserted into the introducing tube;

at least two or more clips each having a proximal end portion, the clips each forming a pinch section at a distal end of an arm section that extends from the proximal end portion and having an opening/expanding property, wherein a plurality of clips are arranged in series in the introducing tube, and a compression member is movably inserted backwardly into a clip mounted in the most proximal end portion of the inside of the introducing tube.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiment of the invention, and together with the general description given above and the detailed description of the embodiment given below, serve to explain the principles of the invention.

FIG. 1A is a longitudinal side section showing a distal end portion of a apparatus for ligating living tissues according to a first embodiment of the present invention;

FIG. 1B is a sectional view taken along the line A-A of FIG. 1A;

FIG. 8A is a longitudinal side view showing a distal end portion in a apparatus for ligating living tissues according to a third embodiment of the present invention;

FIG. 8B is a sectional view taken along the line E-E of FIG. 8A;

FIG. 10A is a plan view showing a clip according to the present embodiment;

FIG. 10B is a side view showing a clip according to the present embodiment;

FIG. 10C is a view seen in a direction indicated by the arrow D of FIG. 10B;

FIG. 10D is a view seen in a direction indicated by the arrow E of FIG. 10B;

FIG. 11 is a perspective view showing a clip tightening ring according to the present embodiment;

FIG. 12 is a perspective view showing a clip unit in a partially cutout manner according to the present embodiment;

FIG. 13 is a side view showing a state in which a clip is retained in a living tissue according to the present embodiment;

FIG. 14A is a longitudinal side section showing a apparatus for ligating living tissues according to a fourth embodiment of the present invention;

FIG. 14B is a sectional view taken along the line F-F of FIG. 14A;

FIG. 15A is a longitudinal side section showing a apparatus for ligating living tissues according to a fifth embodiment of the present invention;

FIG. 15B is a sectional view taken along the line G-G of FIG. 15A;

FIG. 16 is a perspective view showing a compression member according to the present embodiment;

FIG. 23A is a longitudinal side section showing a distal end portion of a apparatus for ligating living tissues according to a tenth embodiment of the present embodiment;

FIG. 23B is a longitudinal plan section showing a distal end portion of a apparatus for ligating living tissues according to the tenth embodiment of the present embodiment;

FIG. 23C is a sectional view taken along the line H-H of FIG. 23B;

FIG. 23D is a sectional view taken along the line I-I of FIG. 23B;

FIG. 23E is a sectional view taken along the line J-J of FIG. 23B;

FIG. 27A is a longitudinal side section showing an introducing tube connecting portion according to the present embodiment;

FIG. 27B is a sectional view taken along the line K-K of FIG. 27A;

FIG. 28A is a longitudinal side section showing a manipulating portion with a ratchet according to the present embodiment;

FIG. 28B is a sectional view taken along the line L-L of FIG. 28A;

FIG. 28C is a sectional view taken along the line M-M of FIG. 28A;

FIG. 29A is a longitudinal side section showing a manipulating portion with a racket according to the present embodiment;

FIG. 29B is a sectional view taken along the line N-N of FIG. 29A;

FIG. 29C is a sectional view taken along the line O-O of FIG. 29A;

FIG. 32A is a longitudinal side section showing an introducing tube when five clips are mounted on the introducing tube according to another embodiment of the present invention; and FIG. 32B is a sectional view taken along the line P-P of FIG. 32A.

DETAILED DESCRIPTION OF THE INVENTION

Figure 2A:
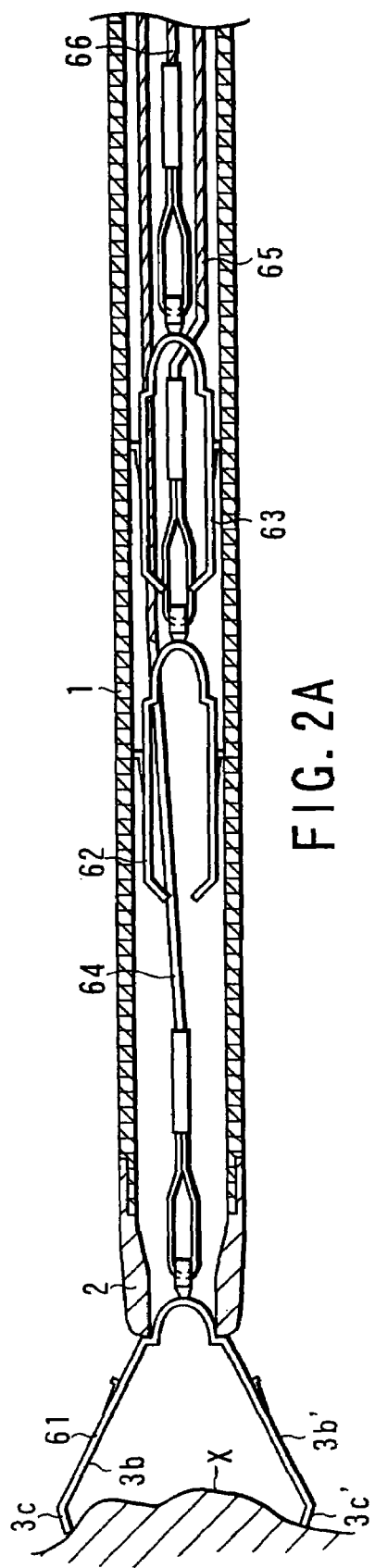
FIG. 2A to FIG. 2C are views each illustrating working according to the present embodiment.

Hereinafter, preferred embodiments of the present invention will be described with reference to the accompanying drawings.

FIG. 1A and FIG. 1B to FIG. 5A and FIG. 5B each show a first embodiment. An introducing tube 1 has its flexibility such that the tube can be inserted into a channel of an endoscope. A distal end tip 2 is provided at a distal end portion of this introducing tube 1. This distal end tip 2 is fixed at the distal end portion of the introducing tube 1 by means of welding, adhesive or press-fit. A manipulating wire 4 is movably inserted into the introducing tube 1, and a clip 3 which can be freely protruded and recessed from the distal end portion of the introducing tube 1 is removably connected to the distal end portion of this manipulating wire 4.

The introducing tube 1 is provided as a coil sheath with its irregularities on the internal and external faces on which a metallic wire whose section is round shaped (such as a stainless wire) is closely wound. This tube is configured so that a sheath is not broken even if a force of compressing a sheath is applied to a sheath distal end portion and a sheath proximal end portion.

In addition, the manipulating member 1 may be a rectangular coil sheath whose internal and external faces are flat on which a metallic wire (such as a stainless wire) whose sectional face is round is crushed, and the sectional face of the wire is rectangular and is closely wound. In this case, its internal face its flat, and thus, the clip 3 can be easily protruded, and the manipulating wire 4 can be easily inserted. In addition, even if the same wire element diameter is used, a coil sheath with its large internal diameter dimension can be provided as compared with such a round shaped coil sheath. In this manner, the clip 3 can be protruded more easily, and the manipulating wire 4 can be inserted more easily.

Further, the introducing tube 1 may be a tube sheath made of, for example, a polymeric resin (such as synthetic polymeric polyamide, high density/low density polyethylene, polyester, polytetrafluoro ethylene, tetrafluoro ethylene-perfluoroalkyl vinyl ether copolymer, or tetrafluoro ethylene-hexafluoro propylene copolymer and the like). In this case, the sheath internal and external faces have slipping properties so as to facilitate insertion into, or removal from an endoscope channel, protrusion of the clip 3, or insertion of the manipulating wire 4.

In addition, the introducing tube 1 may be a double tube having an inner layer and an outer layer at its wall section, and may be a tube sheath embedded: by a reinforce member interposing between the double tubes. In this case, the inner layer and outer layer are formed of the polymeric resin. The reinforce member is formed of a cylindrically shaped blade knitted in a lattice shape with a thin metal wire, for example. In this manner, even when a force of compressing a sheath against a distal end portion and a proximal end portion of the sheath, the sheath is not broken because of its excellent compression resistance as compared with a tube sheath in which the reinforce member is not embedded.

The dimensions of the introducing tube 1 are as follows. That is, the introducing tube has its outer diameter such that the tube can be inserted into an endoscope channel. The thickness of the sheath is determined depending on rigidity of the element material. The thickness of the metallic sheath is about 0.2 mm to 0.7 mm, and the polymeric resin-based tube is about 0.3 mm to 0.8 mm. There is an advantage that the thickness can be reduced, and the inner diameter of the sheath can be increased by embedding the reinforce member.

The distal end tip 2 is provided as a metallic short tube (such as a stainless tube), its outer periphery face is formed in a tapered shape, and its distal end portion is convergent. This makes it easy to insert the introducing tube 1 into the endoscope channel. In addition, the inner periphery face is tapered, and the clip 3 can be easily protruded from the distal end tip 2. In addition, the inner diameter of the distal end portion of he distal end tip 2 is dimensionally defined so that projections provided with an arm section of the clip 3 described later are engaged, and the arm section of the clip 3 can be opened. The outer diameter of the most distal end of the distal end tip 2 is about 1.5 mm to 3.3 mm in diameter, and the inner diameter of the most distal end of the distal end tip 2 is about 1.0 mm to 2.2 mm in diameter.

At the clip 3, as shown in FIG. 3A to FIG. 3D, a thin metallic band plate is bent at its center portion, and its bent portion is formed as a proximal end portion 3a. Both arm sections 3b and 3b' extending from this proximal end portion 3a are bent in a expanding/opening direction. Further, the distal end rim portions of these arm sections 3b and 3b' each are bent so as to face to each other, and are formed as pinch sections 3c and 3c'. One of the distal ends of the pinch sections 3c and 3c', is formed as a protrusion shape 3d so as to pinch a living tissue X (refer to FIG. 2B and FIG. 5), and the other is formed as a recess shape 3e. Then, opening/expanding properties are imparted to the arm sections 3b and 3b' so as to open the pinch section 3c. A backwardly protruding hook 3f is mounted on the proximal end portion 3a. At this hook 3f, a stainless-based thin plate extending from the proximal end portion 3a is bent in a substantially J shape.

At the arm sections 3b and 3b' respectively, there are provided projections 3g and 3g' that can be engaged with the distal end tip 2 (when the clip proximal end portion is introduced into the distal end tip) when the clip 3 is ligated.

A thin band plate of the clip 3 is made of stainless having its resilience, thereby making the plate rigid and making it possible to reliably pinch a living tissue.

For example, expanding/opening properties are imparted to the arm sections 3b and 3b' by applying an ultra-elastic alloy such as a nickel titanium alloy thereto, whereby the arm sections 3b and 3b' open more reliably when they are protruded from the sheath.

If a tensile stress quantity of about 1 kg to 5 kg is applied to the hook 3f provided at the proximal end portion of the clip 3, the hook 3f cannot maintain in its J shape, and is deformed to be extended in a substantially I shape.

In addition, the thickness of the band plate of the clip 3 is 0.15 mm to 0.3 mm, and the plate width of the pinch sections 3c and 3c' each is 0.5 mm to 1.2 mm. The plate width of the arm sections 3b and 3b' each is 0.5 mm to 1.5 mm. The size of the protrusions 3g and 3g' each is 0.2 mm to 0.5 mm. The plate width of the proximal end portion 3a is 0.3 mm to 0.5 mm. The hook 3f is protruded with a length of about 1 mm to 3 mm from the proximal end portion 3a of the clip 3.

Figure 4:
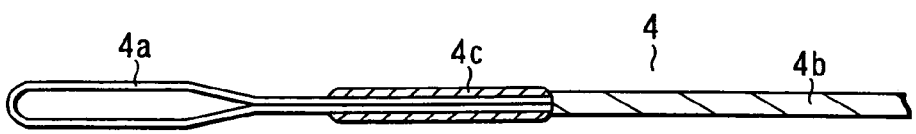
FIG. 4 is a sectional view showing a manipulating wire according to the present invention.
Figure 5A:
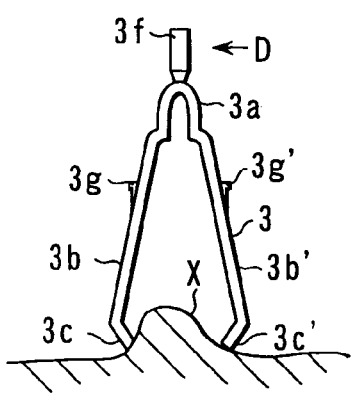
FIG. 5A is a side view showing a state in which a clip is retained in a living tissue according to the present embodiment.
Figure 5B:
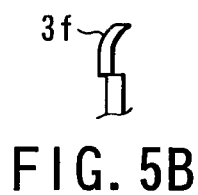
FIG. 5B is a view seen in a direction indicated by the arrow D of FIG. 5A.

The manipulating wire 4 is composed of a loop wire 4a and a proximal end wire 4b, as shown in FIG. 4. A closed loop wire 4a is molded at a distal end of the proximal end wire 4b composed of a twisted metallic wire. Only one twisted wire of the proximal end wire 4b is provided to form the loop wire 4a.

The loop wire 4a and proximal end wire 4b may be bonded with each other via a metallic connecting pipe 4c by means of welding or adhesive. Alternatively, after a closed loop has been formed by one twisted proximal end wire 4b, the wire may be twisted again into the proximal end wire 4b. By molding a loop in this manner, the loop can be molded without interposing specific bonding parts at a bonding portion between the loop wire 4a and manipulating wire 4 and without providing a hard portion.

The outer diameter of an engaging portion between the loop wire 4a and manipulating wire 4 is not increased. Thus, when an attempt is made to minimally reduce the outer diameter of the manipulating wire 4, this bonding is very effective. As described later, when a plurality of clips 3 are mounted in the introducing tube 1, a clearance in the introducing tube 1 is very small. Thus, it is effective to use this wire. The loop wire 4a is hooked by a hook section 3f provided at the proximal end portion 3a of the clip 3, and is engaged with the clip 3.

The manipulating wire 4 is provided as a stainless-based twisted wire. This twisted wire is, more flexible than a single wire, and thus, flexibility of the introducing tube 1 itself is not degraded. In addition, by providing the twisted wire, the wire can be disposed at an arbitrary location in the introducing tube 1 by using such flexibility. This makes it easy to insert the wire into the introducing tube 1 and makes it easier to protrude and ligate the clip 3.

The proximal end wire 4d of the manipulating wire 4 is coated with a polymeric resin (such as synthetic polymeric polyamide, high density/low density polyethylene, polyester, polytetrafluoro ethyelne, tetrafluoro ethylene-perfluoroalkyl vinyl ether copolymer, or tetrafluoro ethylene-hexafluoro propylene copolymer and the like), thereby making it possible to improve manipulating wire slipping properties. The optimal thickness of the coat is about 0.05 mm to 0.1 mm. Further, it is effective to apply emboss processing of 0.01 mm to 0.45 mm to a wire surface in order to improve manipulating wire slipping properties.

A force of 1 Kg to 5 Kg is applied to the loop wire 4a during clip ligation. At this time, it is required to define dimensions so that the loop wire 4a does not break. In addition, the proximal end wire 4b is 0.3 mm or more in outer diameter, and the loop wire 4a is 0.15 mm or more in diameter.

In addition, as shown in FIG. 3A to FIG. 3D, the loop wire 4a at the distal end portion of the manipulating wire 4 is engaged with the hook 3f provided at the proximal end portion 3a of the clip 3, and a clip unit 5 is formed.

Parts configured as described above are incorporated in the introducing tube 1, as shown in FIG. 1A and FIG. 1B. That is, in the introducing tube 1, three clip units 5 are disposed to be arranged in series. However, the number of clip units 5 is not limited to three, and many more clip units 5 may be mounted in the introducing tube 1.

For clarity, the clip units 5 mounted in the introducing tube 1 are named as follows. A clip 61, clip 62, and clip 63 are mounted in order from the most distal end. Manipulating wires engaged with the clips 61, 62, and 63 are defined as a manipulating wire 64, a manipulating wire 65, and a manipulating wire 66.

The manipulating wires 64, 65, and 66 engaged with the clips 61, 62, and 63, respectively, in the introducing tube 1 extend to the proximal end portion of the introducing tube 1. The manipulating wire 64 is disposed in the introducing tube 1 so as to avoid interference with the clips 62 and 63. In addition, the manipulating wire 65 is disposed in he introducing tube 1 so as to avoid interference with the clip 63. FIG. 1B is a sectional view showing the clip 63 disposed at the most distal end. In order to avoid interference with the arm sections 3b and 3b' of the clip 63, the manipulating wires 64 and 65 are disposed in a direction vertical to the opening direction of the arms 3b and 3b' of the clip 63. This makes it easy to insert the manipulating wires 64, 65 and 66 into the introducing tube 1, and makes it easier to protrude the clips 61, 62, and 63 and carry out ligation work.

Now, working of a first embodiment will be described here.

The introducing tube 1 of the clipping apparatus is introduced into a body cavity via the channel of the endoscope inserted into the cavity. A distal end portion of the introducing tube 1 is located in close proximity to a clipping target tissue X, as shown in FIG. 2A. The clip 61 mounted in the introducing tube 1 is protruded outside of the introducing tube 1. The manipulating wire 64 engaged with the clip 61 is extruded in the distal end direction of the introducing tube 1, thereby making it possible to protrude only the clip 61 from the distal end tip 2.

Figure 2B:
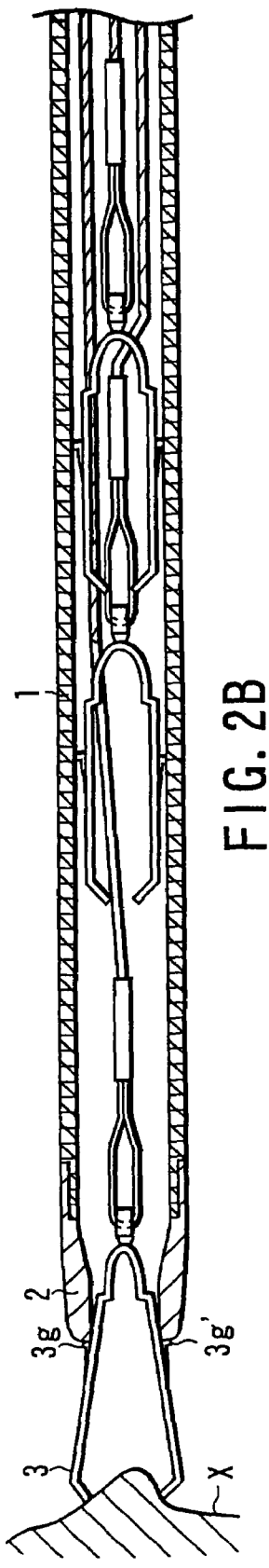

At the clip 61 protruded from the distal end tip 2, opening/expanding properties are imparted to the arm sections 3b and 3b' so as to open the pinch sections 3c and 3c'. Thus, the clip is protruded from the distal end tip 2, and the pinch sections 3c and 3c' open. Then, while the pinch sections 3c and 3c' are pushed against the clipping target tissue X, the manipulating wire 64 is retracted. Then, the proximal end portion 3a of the clip 61 is introduced into the distal end tip 2, as shown in FIG. 2B, and projections 3g and 3g' provided at the arm sections 3b and 3b' of the clip 61 are engaged with a distal end face of the distal end tip 2. When the manipulating wire 64 is further retracted, the proximal end portion 3a of the clip 61 is plastically deformed. Then, the pinch sections 3c and 3c' are closed, whereby the clipping target tissue X can be pinched.

Then, the manipulating wire 64 is further retracted, and a traction force is applied to the hook 3f mounted on the proximal end portion 3a of the clip 61. In this manner, the hook 3f bent in a J letter is expanded, and the loop wire 4a is separated from the hook 3f. Then, the manipulating wire 64 and clip 61 are completely separated from each other. This makes it possible to retain the clip 61 in a living tissue in a body cavity.

Figure 2C:
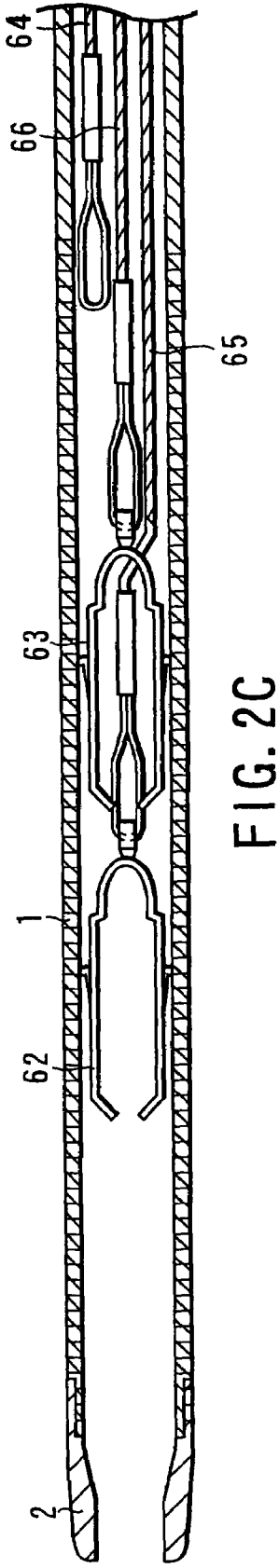
Figure 3A:
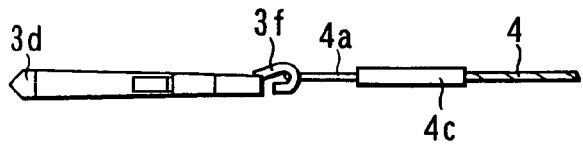
FIG. 3A is a plan view showing a clip according to the present embodiment.
Figure 3B:
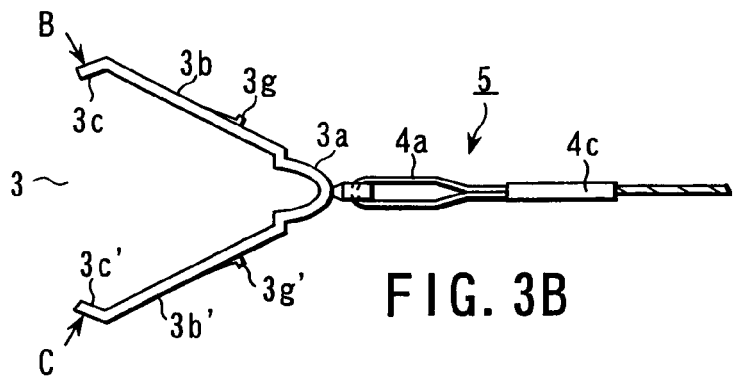
FIG. 3B is a side view showing the clip according to the present embodiment.
Figure 3C:
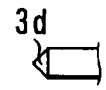
FIG. 3C is a view seen in a direction indicated by the arrow B of FIG. 3B.
Figure 3D:
FIG. 3D is a view seen in a direction indicated by the arrow C of FIG. 3B.

Then, as shown in FIG. 2C, the manipulating wire 64 separated from the clip 61 is retracted to a location free of interference with the backwardly mounted clips 62 and clip 63 in order to retain the clip 62 in a living tissue in a body cavity.

The separated manipulating wire 64 is thus retracted, thereby making it more easy to carry out the subsequent protruding manipulation of the clips 62 and 63. After doing this, the manipulating wire 65 engaged with the clip 62 is extruded in the distal end direction of the introducing tube 1, thereby making it possible to protrude only the clip 62 from the distal end tip 2.

The subsequent manipulation is completely identical to a manipulation for retaining the clip 61 in a living tissue. Then, the clip 62 can be retained in the living tissue. The same manipulation is further repeated, thereby making it possible to retain a plurality of clips 61, 62, and 63 mounted in the introducing tube 1 in a living tissue in a body cavity.

According to a first embodiment, a plurality of clips mounted in an insert tube can be continuously retained in a body cavity by inserting the clipping apparatus in the cavity only one time. Therefore, it is unnecessary to do a complicated work that the clipping apparatus is introduced from the forceps channel or the like to the outside of the cavity every time one clip is retained in the cavity, and a clip must be mounted and inserted again into the cavity. In this manner, a surgical operation time can be reduced, and a burden on a patient can be reduced.

In addition, the manipulating wires are connected to the clips, respectively, making it possible to retain the clips at a tissue in a body cavity one by one in order speedily, easily, and reliably.

Figure 6:
FIG. 6 is a side view showing a manipulating wire according to a second embodiment of the present invention.

FIG. 6 and FIG. 7A to FIG. 7K each show a second embodiment. FIG. 6 is a side view showing a manipulating wire. FIG. 7A to FIG. 7J each show a method for manufacturing a manipulating wire.

As shown in FIG. 6, a manipulating wire 7 comprises a loop wire 7a and a proximal end wire 7b. The proximal end wire 7b is composed of a twisted metallic wire. For example, this wire is twisted with three element wires.

Now, a method for manufacturing the manipulating wire 7 (for example, manufacturing method using 1×3 twisted wires) will be described with reference to FIG. 7A to FIG. 7J. The outer diameter of the wire is about 0.3 mm to 0.6 mm in diameter.

Figure 7A:
FIG. 7A to FIG. 7K are views each showing a method for manufacturing a manipulating wire according to the present embodiment.
Figure 7B:
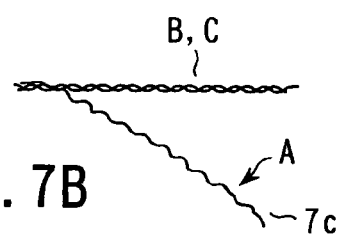
Figure 7C:
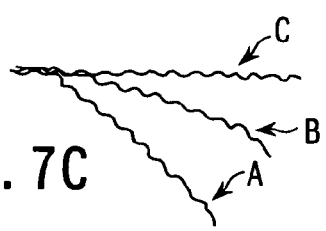
Figure 7D:
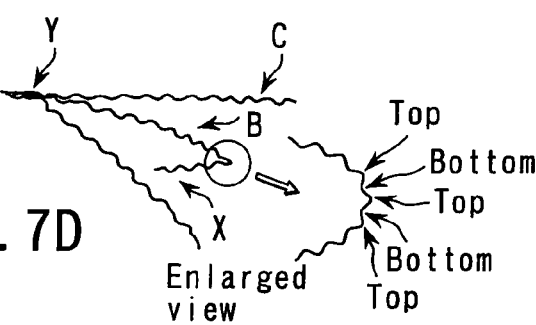
Figure 7E:
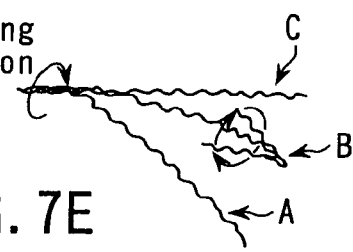
Figure 7F:
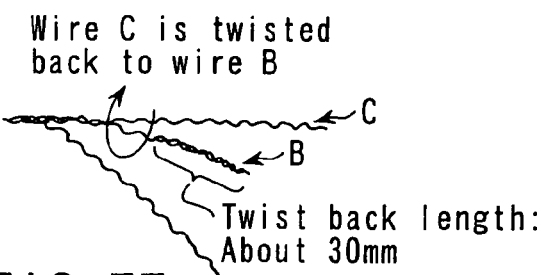
Figure 7G:
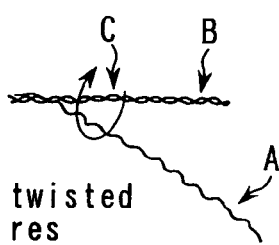

1. A wire end portion 7c is loosened as shown in FIG. 7A.
2. One of the three wires, i.e., wire A is loosened while it is turned, as shown in FIG. 7B. At this time, a length of about 60 mm is loosened from the wire end portion 7c similarly.
3. Second wire B or C is loosened similarly as shown in FIG. 7C. At this time, a length of about 60 mm is loosened from the wire end portion 7c similarly.
4. Second wire B or C is folded as shown in FIG. 7D. At this time, a folded end X and a loosened end Y must be spaced sufficiently from each other. In addition, it is more easier to fold the wire at a top portion when it is rounded, as shown in enlarged view.
5. The folded wire B is turned and twisted in the loosing direction, as shown in FIG. 7E (in the case of Z twisting). At this time, a deformed end portion is cut in advance before twisted. As shown in FIG. 7F, the twist-back length is about 30 mm.
6. As shown in FIG. 7F, wire C is twisted back to wire B, and the wire is cut at a location of the folded end of wire B. At this time, wires C and B are provided so as not to be spaced and superimposed. (This is because wire A easily slips when it is returned).
7. As shown in FIG. 7G, wire A is twisted back to wires B and C. At this time, it is desirable that an abutment portion between wire C and wire B be observed under a substance microscope. In addition, care must be taken so that wire C and wire B do not move when a portion forward or backward of the abutment portion is twisted.

Figure 7H:
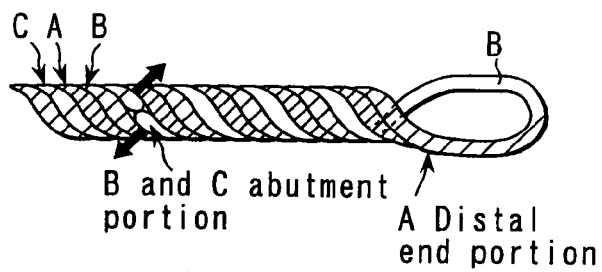

Further, as shown in FIG. 7H, when wire A is loaded, care must be taken so as not to flip wires B and C in a direction indicated by the filled arrow. Wire A is easily loaded by placing the wire at a distal end side (loop side) relevant to the abutment portion of wires B and C.

Figure 7I:
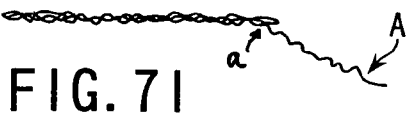
Figure 7J:
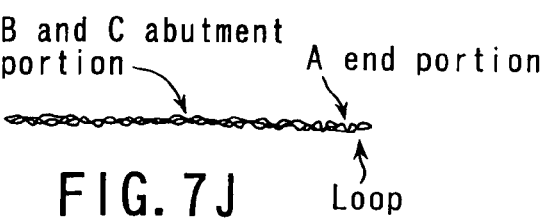

8. As shown in FIG. 7I, wire A is cut at the extremity of the loop (portion "a").
9. As shown in FIG. 7J, cutting is completed. The loop is defined as about 5 mm in length. In addition, the abutment portion of wires B and C and the end portion of wire A may be prevented from looseness of twist by means of welding, adhesive, or any other method.

Working of a second embodiment is identical to that of the first embodiment. A duplicate description is omitted here.

According to the second embodiment, the connecting pipe 4c is not provided, and thus, the manufacturing cost can be reduced as compared with the manipulating wire 4 according to the first embodiment. In addition, the outer diameter is not increased at a bonding portion between the proximal wire 7b and the loop wire 7a as well. Thus, the insert properties of the manipulating wire 4 is maintained without an increase in frictional resistance relevant to the internal face of the introducing tube 1. In this manner, the clip 3 can be easily protruded from the introducing tube 1.

Figure 7K:
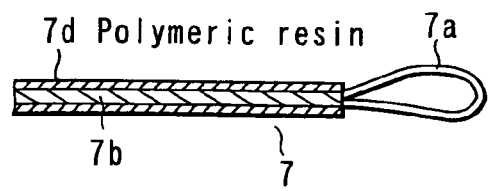
Figure 9A:
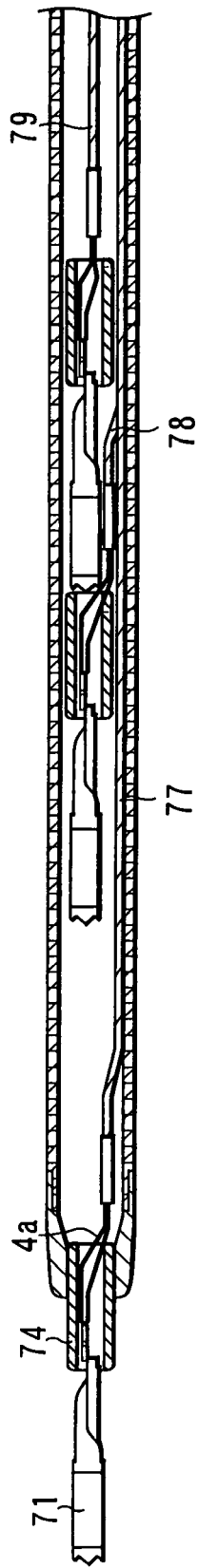
FIG. 9A to FIG. 9C are longitudinal side sections each showing a distal end portion in a living body clipping apparatus according to the present embodiment.
Figure 9B:
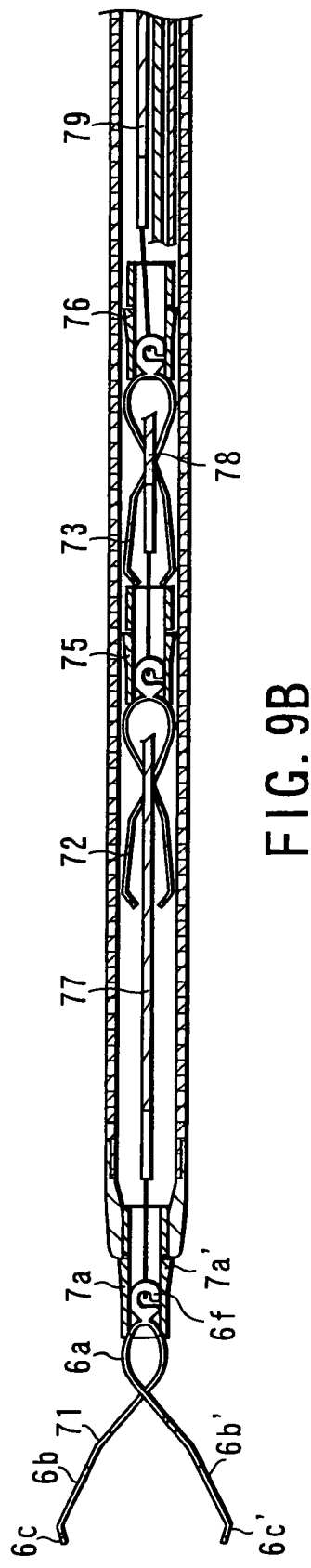
Figure 9C:
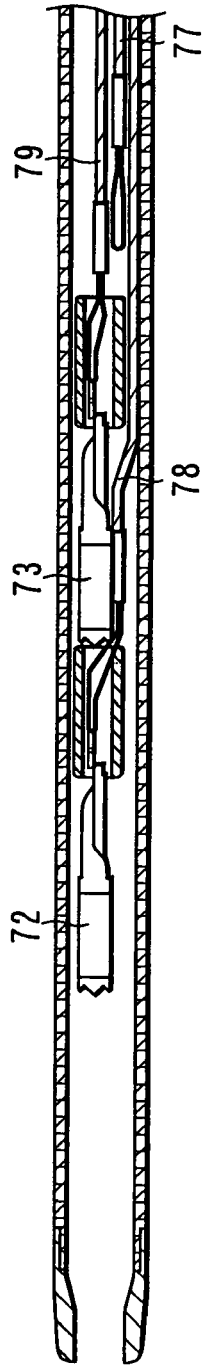

The proximal wire 7b of the wire shown in FIG. 7J is covered with the polymeric resin 7d, whereby the wire slipping properties can be improved. In this manner, a frictional resistance relevant to the internal face of the introducing tube 1 or a sliding resistance between a plurality of wires provided in the introducing tube can be reduced, thus making it easy to protrude a clip, and ligation can be carried out with smaller force. FIG. 7K shows a coat wire.

The polymeric resin 7d is properly made of a synthetic polymeric polysmide, high density/low density polyethylene, polyester, polytetrafluoro ethylene, tetrafluoro ethylene-perfluoroalkyl vinyl ether copolymer, a tetrafluoro ethylene-hexafluoro propylene copolymer or the like. The thickness of the coat is optimally about 0.05 mm to 0.1 mm. Further, in order to improve slipping properties of the manipulating wire, it is effective to apply emboss processing of 0.01 mm to 0.45 mm to the wire surface.

FIG. 8A and FIG. 8B to FIG. 13 each show a third embodiment. Like constituent elements in the first embodiment are designated by like reference numerals. A duplicate description is omitted here.

The introducing tube 1 and manipulating wire 4 are identical to those according to the first embodiment. A distal end tip 2 is welded, adhered, or press-fitted at a distal end of the insert tube 1. The distal end tip 2 is formed by a short tube made of a metal (such as stainless), the outer periphery face is formed in a tapered shape, and the distal end portion is convergent. Therefore, the introducing tube 1 can be inserted into the endoscope channel. In addition, the inner periphery face of the distal end tip 2 is formed in a tapered shape, and the inner diameter of the distal end portion is dimensionally substantially identical to the outer diameter of the clip tightening ring 8 described later. In this manner, a play of the clip tightening ring 8 is suppressed.

In addition, the outer diameter of the most distal end of the distal end tip 2 is 1.5 mm to 3.3 mm in diameter. The inner diameter of the most distal end of the distal end tip 2 is about 1.0 to 2.2 mm in diameter.

Now, a description of clip 9 will be described with reference to FIG. 10A to FIG. 10D. A thin metallic band plate is bent at its center portion, and the bent portion is formed as a proximal end 9a. Both arm sections 9b and 9b' extending from this proximal end portion 9a cross each other. Therefore, the proximal end portion 9a of the clip 9 is formed in a substantially oval shape. Further, the distal end portions of the arm sections 9b and 9b' are bent so as to face to each other, and the bent portions are defined as pinch sections 9c and 9c'. One of the distal end of the pinch sections 9c and 9c' is formed as a protrusive shape 9d and the other is formed as a recess shape 9e in order to easily pinch a living tissue. Then, opening/expanding properties are imparted to the arm sections 9b and 9b' so as to open the pinch sections 9c and 9c'. A backwardly protruded deformable hook 9f is mounted on the proximal end portion 9a. This hook 9f is provided by molding the band plate, in advance, in a J shape, and then, folding the plate at the proximal end portion.

In this clip 9, for example, a thin band plate is made of stainless, is rigid, and is capable of reliably pinching a living tissue. For example, this plate may be made of an ultra-elastic alloy such as a nickel titanium alloy. The expanding/opening properties are imparted to the arm sections 9b and 9b', whereby the arm sections 9b and 9b' open more reliably when they are protruded from the introducing tube 1.

When a tensile stress quantity of about 1 Kg to 5 Kg provided at the proximal end portion 9a of the clip 9 is applied, the hook 9f cannot be maintained in a J shape. This hook is deformed, and extends in a substantial I shape.

At the hook 3f of the clip 3 according to the first embodiment, a stainless-based thin plate extending from the proximal end portion 3a is formed to be bent, and is molded in a J shape. Thus, there has been a problem that the force quantities when the hook 3f is deformed are different from each other due to a deviation caused by processing. However, the hook 9f in the clip 9 according to the present embodiment is formed to be bent at the proximal end portion 9a of the clip 9. Thus, there is an advantage that the force quantity when the hook 9f is deformed can be stabilized.

The thickness of the band plate forming this clip 9 is 0.15 mm to 0.3 mm. The plate thickness of the pinch sections 9c and 9c' each is 0.5 mm to 1.2 mm. The plate width of the arm sections 9b and 9b' each is 0.5 mm to 1.5 mm. The hook 9f is protruded from the proximal end portion 9a with a length of about 1 mm to 3 mm.

Now, a description of clip tightening ring 8 will be given with reference to FIG. 11. This ring is molded of a resin or a metal having rigidity and elasticity. A pair of two blades 8a and 8a' that are elastically deformed and disposed to be freely protruded and recessed in the circumferential direction are provided at the outer periphery portion of the ring. The number of blades 8a and 8a' is not limited to a pair or two, and may be three or four. If an external force is applied to the circumferential face of the ring in vertical direction, the blades 8a and 8a' are folded in the internal face of the ring. The blades 8a and 8a' come into contact with the internal face of the introducing tube 1 and the internal face of the distal end tip 2, and thus, are formed as inclined faces 8b and 8b' at the distal end side. Thus, these blades can be extruded smoothly and without resistance.

The clip tightening ring 8 is engagingly mounted on the arm sections 9b and 9b' of the clip 9, thereby closing the arm sections 9b and 9b' of the clip 9. This ring is formed in a substantially tubular shape. The clip 9 and manipulating wire 4 are engaged with each other by hooking the loop wire 4a on the hook 9f. As shown in FIG. 12, even if the clip 9 is extruded by means of the manipulating wire 4, a polymeric material 8c such as silicone is engaged into the clip tightening ring 8 in order to maintain engagement between the clip 9 and the manipulating wire 4 and to temporarily fix the clip 9 and clip tightening ring 8 to each other.

The blades 8a and 8a' of the clip tightening ring 8 may be mounted in the introducing tube 1 while they are folded. However, the blades 8a and 8a' are mounted in the introducing tube 1 in a protruded state, whereby elasticity of the blades 8a and 8a' can be maintained over a longer period. In addition, a contact area between the internal face of the introducing tube 1 and the blades 8a and 8a' each is reduced, and thus, the protrusion force quantity of the clip 9 can be reduced.

The clip tightening ring 8 is formed by injection molding a rigid resin (such as polybutyl terephthalate, polyamide, polyphenylamide, a liquid crystal polymer, polyether ketone, or polyphthalic amide). This ring may be molded by injection molding, cut processing, or plastic processing of an elastic metal (stainless or ultra-elastic alloy such as nickel titanium alloy).

The clip tightening ring 8 is about 0.6 mm to 1.3 mm in inner diameter, and is about 1.0 mm to 2.1 mm in outer diameter. The most outer diameter portion when the blades 8a and 8a' are protruded is 1 mm or more, considering engagement with the distal end tip 2.

Now, a description of a clip unit 10 will be given with reference to FIG. 12. The clip 9 is engagingly fitted into the clip tightening ring 8, and the loop wire 4a at the distal end portion of the manipulating wire 4 is engaged with the hook 9f provided at the proximal end portion 9a of the clip 9. A polymeric material 8c such as silicone is engaged into the clip tightening ring 8 so that engagement between the clip tightening ring 8 and clip 9 and the hook 9f and loop wire 4a is not easily separated. The clip 9 is engagingly fitted into the clip tightening ring 8 so that the opening direction of the arm sections 9b and 9b' of the clip 9 coincides with the direction of the two blades 8a and 8a' provided on the clip tightening ring 8.

Parts configured as described above are incorporated in the introducing tube 1 as follows. That is, in the introducing tube 1, three clip units 10 are disposed to be arranged in series. However, the number of clip units 10 is not limited to three, and many more clip units 10 may be mounted in the introducing tube 1. In FIG. 8A, although three clips 9 are configured, many more clips 9 may be mounted as long as a space in the introducing tube 1 is permitted. That is, four or more clips 9 may be mounted as long as the space in the introducing tube 1 is sufficiently provided.

For clarity, the clip units 10 mounted in the introducing tube 1 are named as follows. A clip 71, clip 72, and clip 73 are named in order from the clip mounted at the most distal end. Clip tightening rings having the clips 71, 72, and 73 engagingly fitted thereto, respectively, are defined as clip tightening rings 74, 75 and 76. Manipulating wires engaged with the clips 71, 72, and 73, respectively, in the clip tightening rings are defined as manipulating wires 77, 78, and 79.

In the introducing tube 1, the manipulating wires 77, 78, and 79 extending from the respective clips 71, 72, and 73 extend to the proximal end portion of the introducing tube 1. The manipulating wire 77 is disposed in the introducing tube 1 so as to avoid interference with the clips 72 and 73. In addition, the manipulating wire 78 is disposed in the introducing tube 1 so as to avoid interference with the clip 73. The manipulating wires 77 and 78 are disposed in a direction vertical to the opening direction of the arm sections 9b and 9b' of the clip 73 in order to avoid interference with the arm sections 9b and 9b' of the clip 73.

FIG. 8B is a sectional view showing a clip tightening ring 76 disposed at the most distant end portion. As shown in the figure, the manipulating wires 77 and 78 are disposed in the introducing tube 1 so as to avoid interference with the blades 8a and 8a' of the clip tightening ring 76, and extend to the proximal end portion. The manipulating wires 77, 78, and 79 are disposed as described above, thereby making it easy to insert the manipulating wires 77, 78, and 79 into the introducing tube 1 and making it easier to protrude or ligate the clips 71, 72, and 73.

Now, working of a third embodiment will be described here.

A distal end of the introducing tube 1 is guided to a target site while the inside of a body cavity is observed by means of an endoscope. A clip 71 mounted in the introducing tube 1 is protruded outside of the introducing tube 1. The manipulating wire 77 engaged with the clip 71 is extruded in the distal end direction of the introducing tube 1, thereby making it possible to protrude only the clip 71 and clip tightening ring 74 from the distal end tip 2. The blades 8a and 8a' of the clip tightening ring 74 are folded in the clip ring tightening ring 74 when they pass through the inside of the distal end tip 2. When these blades 8a and 8a' pass through the distal end tip 2, the blades are protruded again. In this manner, the clip tightening ring 74 can be prevented from entering the distal end tip 2 again.

After it is checked that the blades 8a and 8a' of the clip tightening ring 74 are protruded from the introducing tube 1, the manipulating wire 77 is retracted. Then, the blades 8a and 8a' of the clip tightening ring 74 are engaged with an end face of the distal end tip 2. When the manipulating wire 77 is retracted, an oval portion of the proximal end portion 9a of the clip 71 is introduced into the clip tightening ring 74. Here, the oval portion of the proximal end portion 9a is dimensionally greater than the inner diameter of the clip tightening ring 74. Thus, the oval portion is crushed by the clip tightening ring 74. Then, the arm sections 9b and 9b' open significantly in outer diameter. In this state, the clip 71 is guided so as to pinch a target living tissue, and the pinch sections 9c and 9c' of the clip 71 are pushed against the clipping target tissue X. When the manipulating wire 77 is further retracted, the arm sections 9b and 9b' of the clip 71 are introduced into the clip tightening ring 74. Then, the pinch sections 9c and 9c' of the clip 71 is closed, thereby making it possible to pinch the living tissue. When the manipulating wire 77 is further retracted, the hook 9f provided at the proximal end portion 9a of the clip 9 is extended, and engagement between the clip 71 and manipulating wire 77 is released. In this way, the clip 71 can be retained at a living tissue in the cavity, as shown in FIG. 13.

Then, in order to retain the clip 72 at the living tissue in the body cavity, the manipulating wire 77 separated from the clip 71 is retracted to a position at which the wire does not interfere with the backwardly mounted clip 73 and clip tightening ring 76. In this way, the separated manipulating wire 77 is retracted, thereby making it easier to protrude the clip 72 and clip 73.

In this state, the manipulating wire 78 of the clip 72 is extruded in the distal end direction of the introducing tube 1, thereby making it possible to protrude only the clip 72 and clip tightening ring 75 from the distal end tip 2.

The subsequent manipulation is completely identical to that for retaining the clip 71 at the living tissue. Then, the clip 72 and clip tightening ring 75 can be retained at the living tissue.

By further repeating the same manipulation, a plurality of clips 71, 72, and 73 mounted in the introducing tube 1 can be retained at the living tissue in the cavity.

According to the third embodiment, in addition to advantageous effect of the first embodiment, the clip arm section is closed by the clip tightening ring. Thus, the living tissue can be ligated with stronger force.

FIG. 14A and FIG. 14B each show a fourth embodiment. Like constituent elements according to the third embodiment are designated by like reference numerals. A duplicate description is omitted here.

A construction of the present embodiment is identical to that of the third embodiment except that a compression member 11 is added in the construction of the third embodiment.

The compression member 11 has flexibility that the member can be inserted into the introducing tube 1, and is disposed backwardly of a clip tightening ring 76 mounted at the most proximal end portion in the introducing tube 1.

The compression member 11 consists of a coil sheath that is irregular on the internal and external faces on which a metallic wire (such as a stainless wire) whose sectional face is round shaped is closely wound. This makes it possible to easily protrude the clip unit 10 from the introducing tube 1.

The compression member 11 may be a rectangular coil sheath whose internal and external faces are flat on which a metallic wire (such as a stainless wire) whose sectional face is round is crushed, and the sectional face of the wire is rectangular and is closely wound. A compression member with its large internal diameter can be achieved even under the condition of the same rigidity as compared with a round shaped coil sheath. In this manner, the manipulating wire 4 can be easily inserted, and the force quantity caused by ligating the clip 9 can be reduced. For example, when the clip is formed by a tube sheath made of a polymeric resin (such as synthetic polymeric polyamide, high density/low density polyethylene, polyester, polytetrafluoro ethylene, tetrafluoro ethylene-perfluoroalkyl vinyl ether copolymer, or tetrafluoro ethylene-hexafluoro propylene copolymer and the like), the internal and external faces of the sheath have slipping properties, thus facilitating insertion into the introducing tube 1 and insertion of the manipulating wire 4. This makes it easy to protrude the clip 9 and makes it possible to reduce the force quantity during ligation of the clip 9.

In addition, the compression member 11 may be a double tube having an internal layer and an external layer at its wall portion, and may be a tube sheath embedded while a reinforce member is interposed between the double tubes. The internal layer and external layer are formed of the above-described polymeric resin. The reinforce member is formed of a cylinder blade or the like knitted with a thin metal wire, for example in a lattice shape. This tube sheath has its excellent compression resistance as compared with a tube sheath in which a reinforce member is not embedded. Thus, the sheath is not broken because of its compression resistance when the clip 9 is protruded.

Further, the compression member 11 has an outer diameter such that the member can be inserted into the introducing tube 1 and an inner diameter such that a plurality of manipulating wires 4 can be inserted. For example, the outer diameter is 3 mm or less in diameter, and the inner diameter is maximally large. However, the thickness is required to be a dimension such that the compression member 11 is not broken, and a force quantity required for protruding the clip 9 can be securely transmitted.

Now, working of a fourth embodiment will be described here.

A distal end of the introducing tube is guided to a target site while the inside of a body cavity is observed by using an endoscope. Then, the clip 71 and the clip tightening ring 74 mounted in the introducing tube 1 are protruded outside of the introducing tube 1. This is achieved by extruding the compression member 11 in the distal end direction in the introducing tube 1. The compression member 11 is inserted backwardly of the clip tightening ring 76 in the introducing tube 1. The force applied by the compression member 11 by extruding the compression member 11 in the distal end direction of the introducing tube 1 is transmitted from the clip tightening ring 76 and clip 73 to the clip tightening ring 75, the clip 72, and then, the clip tightening ring 74 and clip 71. In this way, the clip 71 and clip tightening ring 74 are protruded from the distal end tip 2 by a force applied to the compression member 11.

An operation after the clip 71 and clip tightening ring 74 have been protruded is identical to that according to the first embodiment.

After the clip 71 has been retained into a living tissue, a manipulating wire 77 separated from the clip 71 is retracted to a location free of interference with the clip tightening ring 76 mounted backwardly. Specifically, the manipulating wire 77 is retracted into the internal cavity of the compression member 11. The thus separated manipulating wire 77 is retracted, thereby making it easy to protrude the clip 72 and clip 73.

Working of protruding the clip 72 and clip 73 and retaining these clips at a living tissue is identical to that of the clip 71. By repeating the same operation as that in the clip 71, a plurality of the clips 71, 72, and 73 mounted in the introducing tube 1 can be retained at the living tissue.

According to the present embodiment, the clips can be protruded easily and reliably.

FIG. 15A, FIG. 15B, and FIG. 16 each show a fifth embodiment. Like constituent elements in the third embodiment are designated by like reference numerals. A duplicate description is omitted here. The present embodiment is identical to the third embodiment except that the compression member 12 is added in a construction of the third embodiment.

The compression member 12 has flexibility that the member can be inserted into the introducing tube 1, and the compression member is disposed backwardly of the clip tightening ring 76. In addition, this compression member has a plurality of lumens 12a, 12b, and 12c such that the manipulating wires 77, 78, and 79 can be inserted independently.

The compression member 12 is provided as a tube sheath made of a polymeric resin (such as such as synthetic polymeric polyamide, high density/low density polyethylene, polyester, polytetrafluoro ethylene, tetrafluoro ethylene-perfluoroalkyl vinyl ether copolymer, or tetrafluoro ethylene-hexafluoro propylene copolymer and the like). The manipulating wire 4 extended from a plurality of the clip units 8 is distributed into a plurality of the lumens 12a, 12b, and 12c provided at the compression member 12, and is inserted into the proximal end portion of the compression member 12.

Further, the compression member 12 has an outer diameter such that the member can be inserted into the introducing tube 1. The number of the lumens 12a, 12b, and 12c must be at least equal to or greater than the number of clips. In addition, the inner diameter of the lumens 12a, 12b, and 12c is such that at least one manipulating wire 4 can be inserted. In addition, the outer diameter of the compression member 12 is 3 mm or less in diameter, and the internal diameter of the lumens each is 0.3 mm or more in diameter.

According to the fifth embodiment, the manipulating wires 77, 78, and 79 engaged with the clips 71, 72, and 73 respectively are inserted into a plurality of the lumens 12a, 12b, and 12c provided in the compression member 12, and are guided to the proximal end side of the introducing tube 1. Therefore, the manipulating wires 77, 78, and 79 are inserted while these wires are spaced in the introducing tube 1. Thus, three manipulating wires 77, 78, and 79 are not interfered with each other in the introducing tube 1. In this manner, a sliding frictional resistance among the manipulating wires 77, 78, and 79 decreases in the introducing tube 1. Thus, the traction force quantity can be transmitted to a distal end of the introducing tube 1 without any loss. That is, a ligation work can be carried out with smaller force.

Figure 17:
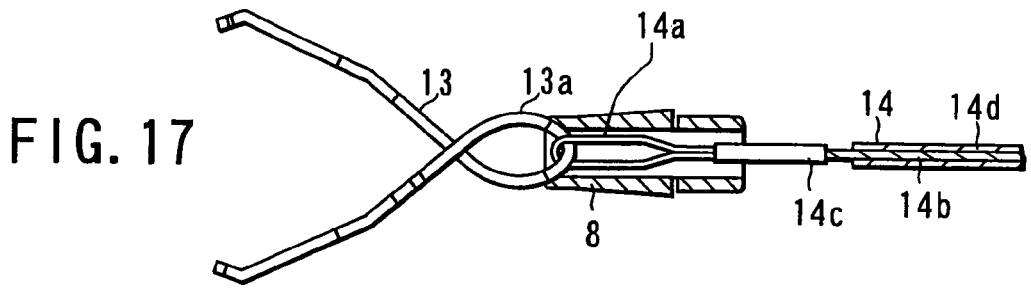
FIG. 17 is a longitudinal cross section showing a clipping apparatus according to a sixth embodiment of the present invention.
Figure 18:
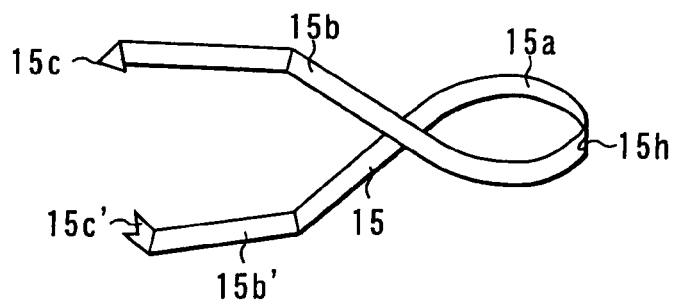
FIG. 18 is a perspective view showing a clip according to a seventh embodiment of the present, invention.
Figure 19A:
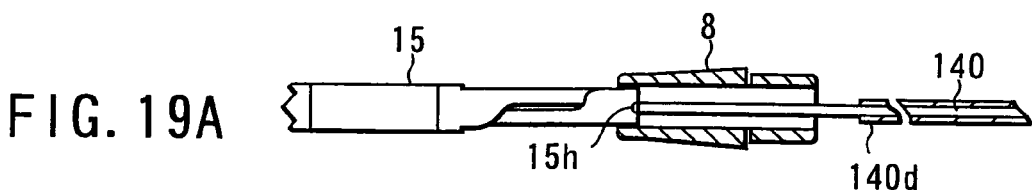
FIG. 19A is a plan view showing a clip according to the present embodiment.
Figure 19B:
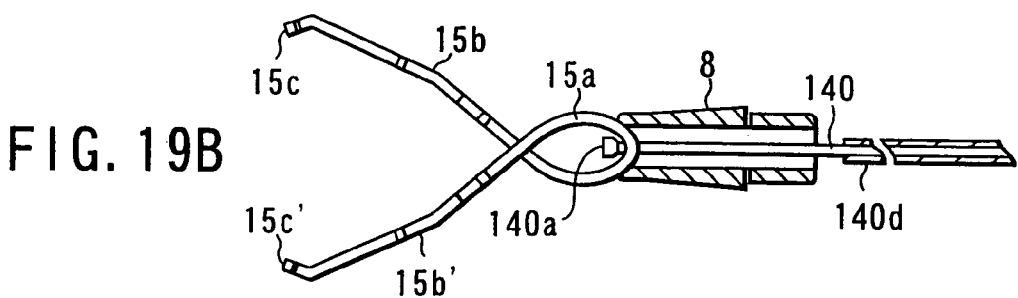
FIG. 19B is a side view showing a clip according to the present embodiment.
Figure 19C:
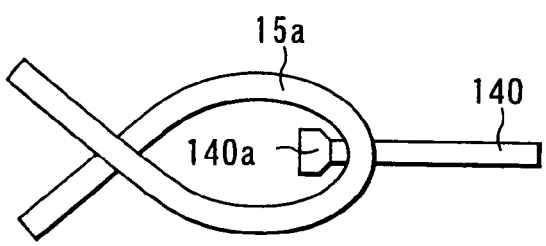
FIG. 19C is an enlarged side view showing a flat inflating portion.
Figure 20A:
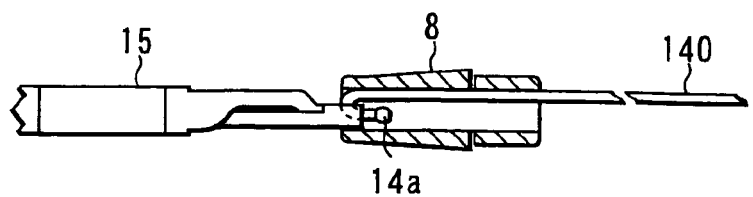
FIG. 20A is a plan view showing a clip according to the present embodiment.
Figure 20B:
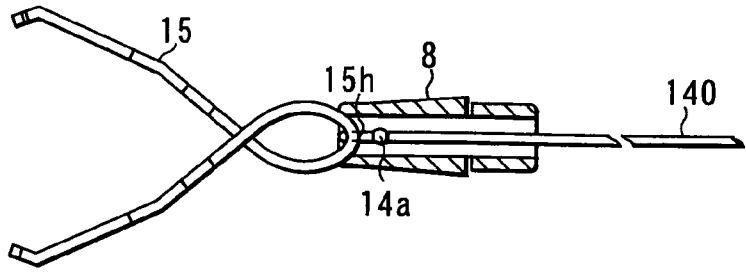
FIG. 20B is a side view showing a clip according to the present embodiment.

FIG. 17 shows a sixth embodiment. The present embodiment is different from the third embodiment in structure of engagement between a clip and a manipulating wire. The clip 13 according to the present invention does not have the hook 6f in the clip 6 according to the third embodiment.

A manipulating wire 14 is composed of a loop wire 14a and a proximal end wire 14b. The loop wire 14a closed at a distal end of a proximal end wire composed of a twisted metallic wire is molded. The loop wire 14a is formed of one twisted proximal end wire 14b. When a twisted core wire is used for the loop wire 14a, assembling properties are excellent. The core wire may be a twisted wire or a single wire. The loop wire 14a and proximal end wire 14b are bonded to be welded or adhered via a metallic connecting pipe 14c.

The manipulating wire 14 is provided as a twisted wire made of stainless. The thus-twisted wire is more flexible than a single wire. Thus, the flexibility of the introducing tube 1 itself is not degraded. The proximal end wire 14b of this manipulating wire 14 is 0.3 mm to 0.6 mm in outer diameter, and the loop wire 14a is about 0.1 mm to 0.2 mm in diameter.

The manipulating wire 14 is coated with a polymeric resin 14d (such as synthetic polymeric polyamide, high density/low density polyethylene, polyester, polytetrafluoro ethylene, tetrafluoro ethylene-perfluoroalkyl vinyl ether copolymer, or tetrafluoro ethylene-hexafluoro propylene copolymer and the like), whereby the slipping properties of the manipulating wire can be improved. The thickness of the coat is optimally about 0.05 mm to 0.1 mm. Further, in order to improve the slipping properties of the manipulating wire, it is effective to apply emboss processing of 0.01 mm to 0.45 mm to the wire surface.

According to the present embodiment, the loop wire 14a is directly engaged with the proximal end portion 13a of the clip 13. A force of 1 Kg to 5 Kg is applied to the loop wire 14a during legation of the clip 13. The loop wire 14a is dimensionally defined to break when the force is applied. The loop wire 14a breaks, whereby the clip 13 and manipulating wire 14 are separated from each other, and the clip 13 can be retained in the living tissue.

In the present embodiment, engagement between the clip 13 and manipulating wire 14 is separated by breakage of the loop wire 14a. As a modified example thereof, in the loop wire described in the second embodiment, the twisted back length of the element wire B is set to be short, and the twisted loop is loosened during ligation, whereby the engagement between the clip and manipulating wire may be separated. The twisted back length is properly about 5 mm to 10 mm.

According to the present embodiment, a clip can be molded more inexpensively because no hook is provided at the proximal end of the clip as compared with the third embodiment.

FIG. 18 to FIG. 20A and FIG. 20B each show a seventh embodiment.

The present embodiment is identical to the first embodiment in construction except a structure of engagement between the clip and manipulating wire. The clip 15 does not have the hook 3f in the clip 3 as shown in the first embodiment, and a hole 15h through which a manipulating wire 140 can be inserted is provided at a proximal end portion 15a.

The manipulating wire 140 is provided as a single metallic wire, and is formed to about 0.2 mm to 0.7 mm in diameter. The manipulating wire 140 is inserted into the hole 15h, and a flat inflating portion 140a serving as a slip proof is molded at the distal end portion of the manipulating wire 140. A method of molding the flat inflating portion 10a includes caulking fit, for example. The diameter of the hole 15h is properly about 0.2 mm to 0.7 mm. A manipulating wire 140 capable of being inserted into this hole 15h is used. The maximum diameter of the flat inflating portion 140a is always greater than the diameter of the hole 15h, and is about 0.25 mm to 1 mm.

The manipulating wire 140 is coated with a polymeric resin 140d (synthetic polymeric polyamide, high density/low density polyethylene, polyester, polytetrafluoro ethylene, tetrafluoro ethylene-perfluoroalkyl vinyl ether copolymer, or tetrafluoro ethylene-hexafluoro propylene copolymer and the like), whereby the slipping properties of the manipulating wire can be improved. The thickness of the coat is optimally about 0.05 mm to 0.1 mm. Further, in order to improve the slipping properties of the manipulating wire, it is effective to apply emboss processing of 0.01 mm to 0.45 mm to the wire surface.

According to the present embodiment, the manipulating wire 140 is retracted while the pinch sections 15c and 15c' are pushed against the target tissue. The arm section of the clip 15 folded in the expanding/opening direction are engaged with the distal end portion of the distal end tip 2. When the manipulating wire 140 is further retracted, the arm sections 15b and 15b' of the clip 15 are introduced into the distal end tip 2. Then, the pinch sections 15c and 15c' are closed, whereby the target tissue can be pinched.

The manipulating wire 140 is retracted, whereby the flat inflating portion 15a at the distal end of the manipulating wire 140 is pulled off from the hole 15h at the proximal end portion 15a of the clip 15. The diameter of the flat inflating portion 140a is deformed and reduced, or alternatively, the hole 15h at the proximal end portion 15a of the clip 15 is deformed and increased, whereby the manipulating wire 140 is separated from the clip 15. This makes it possible to retain the clip 15 in the living tissue.

In addition, as shown in FIG. 20, the distal end of the manipulating wire 140 is looped in the clip tightening ring 8, and the flat inflating portion 14a is provided outside of an oval portion at the proximal end portion 15a of the clip 15, whereby a force quantity of releasing the engagement between the clip 15 and manipulating wire 140 can be increased. In this, manner, when a tissue is closed at the pinch sections 15c and 15c', a large force can be applied to the clip 15. Thus, a strong ligation force can be obtained.

According to the present embodiment, the clip and manipulating wire are directly engaged with each other, whereby the number of parts at an engagement portion between the clip and manipulating wire is reduced. In this manner, the manufacturing cost is reduced. In addition, the clip mounting work during manufacture is facilitated.

Figure 21:
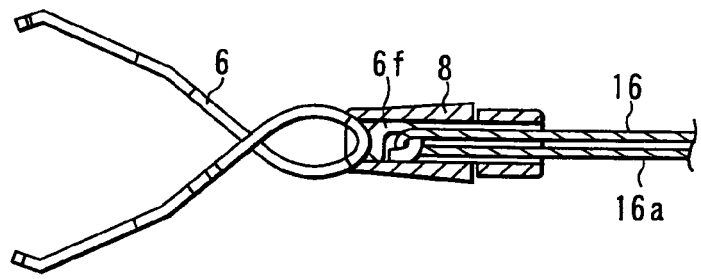
FIG. 21 is a longitudinal side section showing a clipping apparatus according to an eighth embodiment of the present invention.
Figure 22A:
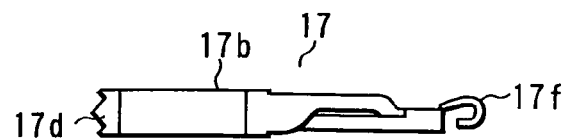
FIG. 22A is a plan view showing a clip according to a ninth embodiment of the present invention.
Figure 22C:
FIG. 22C is a view seen in a direction indicated by the arrow F' of FIG. 22B.
Figure 22B:
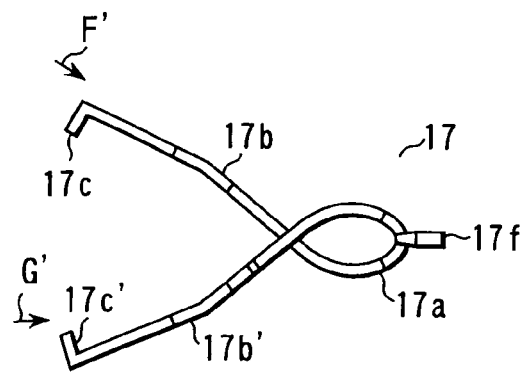
FIG. 22B is a side view showing a clip according to the ninth embodiment of the present invention.
Figure 22D:
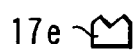
FIG. 22D is a view seen in a direction indicated by the arrow G' of FIG. 22B.

FIG. 21 shows an eighth embodiment. The present embodiment is identical to the third embodiment except a structure of engagement between the clip and manipulating wire.

The manipulating wire 16 is bent at its distal end, and is engaged with a hook 6f of a clip 6. Two manipulating wires 16 are inserted into the proximal end portion of the introducing tube 1. The manipulating wire 16 may be coated with a polymeric resin 16a with its improved slipping properties such as high density/low density polyethylene, for example. The thickness of the coat is optimally about 0.05 mm to 0.1 mm. Further, in order to improve the slipping properties of the manipulating wire 16, it is effective to apply emboss processing of 0.01 mm to 0.45 mm to the wire surface.

The manipulating wire 16 is made of a metallic wire such as a twisted or single stainless wire. The outer diameter is about 0.2 mm to 0.5 mm.

According to the present embodiment, two manipulating wires 16 are retracted together. The other working is identical to that of the third embodiment. According to the present embodiment, the clip and manipulating wire can be engaged with each other more inexpensively as compared with the third embodiment. In addition, by providing a coating, the slipping properties of the manipulating wire is increased, and the frictional resistance relevant with the internal face of the introducing tube is reduced. Then, the traction force quantity can be transmitted to the distal end of the introducing tube without any loss. In this manner, a ligating manipulation can be performed with a small force.

FIG. 22A to FIG. 22D through FIG. 24 each show a ninth embodiment. The introducing tube 1 according to the present embodiment has its outer diameter such that the tube can be inserted into the channel of the endoscope and has its outer diameter that is greater than the outer diameter of the manipulating member described later. The present embodiment is identical to the first embodiment.

At the clip 17 according to the present embodiment, as shown in FIG. 22A to FIG. 22D, a thin metallic band plate is bent at its center portion, and its bent portion is formed as a proximal end portion 17a. Both arm sections 17b and 17b' extending from this proximal end portion 17a are crossed with each other. The proximal end portion 17a is formed in a substantially oval shape.

Further, the distal end rim portions of the arm sections 17c and 17c' each are bent so as to face to each other, and the bent portions are defined as the pinch sections 17c and 17c'. One of distal ends of the pinch sections 17c and 17c' is formed in a protrusive shape 17d and the other is formed in a recess shape 17e in order to easily pinch a living tissue. Then, opening/expanding properties are imparted to the arm sections 17b and 17b so as to open the pinch sections 17c and 17c'. A backwardly-protruded hook 17f is mounted to the proximal end portion 17a. A backwardly-protruded hook 17f is mounted on the proximal end portion 17a. At this hook 17f, a stainless-based thin plate extending from the proximal end portion is bent in a substantially J shape.

At the clip, for example, a material for a thin band plate is formed of a stainless having resilience, is rigid, and is capable of reliably gripping the living tissue. The clip 17 is formed by an ultra-elastic alloy such as nickel titanium alloy, and expanding/opening properties are imparted to the arm sections 17b and 17b', whereby the arm sections 17b and 17b' open reliably when they are protruded from the introducing tube 1.

When a tensile force quantity of about 1 Kg to 5 Kg is applied to the hook 17f provided at the proximal end portion 17a of the clip 17, the hook 17f cannot be maintained in a J shape. Thus, the hook is deformed and expands in a substantially I shape.

Further, in the clip 17, the thickness of the band plate is 0.15 mm to 0.3 mm, and the plate width of the pinch sections 17c and 17c each is 0.5 mm to 1.2 mm. The plate width of the arm sections 17b and 17b' each is 0.5 mm to 1.5 mm. The plate width of the proximal end portion 17a is 0.3 mm to 0.5 mm. The hook 17f is protruded from the proximal end portion 17a of the clip 17 with a length of about 1 mm to 3 mm.

The manipulating wire 18 bonds the manipulating wires in the manipulating wire 16 by using a method such as adhesive or welding, as shown in FIG. 23A. Then, the bonding portion 18b is formed, and a closed loop 18a is formed.

In addition, the manipulating member 19 has flexibility such that the member can be inserted into the introducing tube 1. This manipulating member is disposed backwardly of a clip tightening ring 86 described later, the ring being mounted in the introducing tube 1. During clip ligation, the manipulating member directly receives a force applied by the manipulating wire 18.

The manipulating member 19 is provided as a coil sheath that is irregular on the internal and external faces on which a metallic wire (such as a stainless wire) whose sectional face is round shaped is closely wound. The manipulating member 19 is moved to the distal end side relevant to the introducing tube 1, thereby making it possible to protrude the clip 17 and clip tightening ring 20 from the introducing tube 1.

In addition, the manipulating member 19 may be a rectangular coil sheath whose internal and external faces are flat on which a metallic wire (such as a stainless wire) whose sectional face is round is crushed, and the sectional face of the wire is rectangular and is closely wound. In addition, even if the same element wire diameter is used, a coil sheath with its larger internal diameter can be achieved as compared with a round shaped coil sheath. This makes it easier to protrude the clip 17 and insert the manipulating wire 18.

Further, when the manipulating member 19 is provided as a tube sheath made of a polymeric resin. (such as synthetic polymeric polyamide, high density/low density polyethylene, polyester, polytetrafluoro ethylene, tetrafluoro ethylene-perfluoroalkyl vinyl ether copolymer, or tetrafluoro ethylene-hexafluoro propylene copolymer and the like), the internal and external faces of the sheath have slipping properties, thus facilitating insertion into the introducing tube 1 and insertion of the manipulating wire 18.

For example, when a tube sheath having a metallic wire (such as stainless) embedded in a polymeric resin-based tube sheath is provided, the sheath does not break as compared with a tube sheath in which a wire is not embedded.

The manipulating member 19 has its inner diameter such that the member can be inserted into the introducing tube 1 and its inner diameter such that the manipulating wire 18 an be inserted. The outer diameter is 3 mm or less in diameter. The inner diameter is maximally increased. However, the thickness is required such that a protrusion force quantity can be reliably transmitted, and no breakage occurs even if a force is applied during ligation of the clip 17.

In addition, the clip tightening ring 20 closes arm sections 17b and 17b' by engagingly mounting the ring to the arm sections 17b and 17b' of the clip 17, and is formed in a substantially tubular shape. The clip 17 and manipulating wire 18 are engaged with each other by hooking the loop wire 18a on the hook 18f. The proximal end portion 20a of the clip tightening ring 20 is molded in accordance with a bending angle of the pinch sections 17c and 17c' of the clip 17 so that the pinch sections 17c and 17c' reliably abut against the proximal end portion 20a of the clip tightening ring 20. In this manner, even if a compression force is applied between the clip 17 and manipulating member 19, the clip 17 and clip tightening ring 20 are not inclined, and the reliably-applied compression force can be transmitted to the distal end.

In addition, the clip tightening ring 20 is injection-molded by a rigid resin (such as polybutyterephthalate, polyamide, polyphenyl amide, liquid crystal polymer, polyether ketone, or polyphthalic amid).

In the clip tightening ring 20, for example, an elastic metal (such as stainless) may be molded by injection molding, cutting processing, or plastic processing and the like. The ring is formed so that inner diameter is 0.6 mm to 1.3 mm in diameter, and the outer diameter is 1.0 mm to 2.1 mm in diameter.

Further, in a clip unit 50, a clip 17 is engagingly mounted in a clip tightening ring 20, and a closed loop 18a at the distal end portion of the manipulating wire 18 is engaged with the hook 17f provided at the proximal end portion 17a of the clip 17. A polymeric material 20c such as silicone is engaged into the clip tightening ring 20 so as not to easily separate engagement of the clip tightening ring 20 and the clip 17 and engagement of the hook 17f and the loop wire 17a.

Parts configured as described previously are incorporated in the introducing tube 1 as follows.

In the introducing tube 1, three clip units 50 are disposed to be arranged in series. However, the number of clip units 50 is not limited to three, and many more clip units 50 may be mounted in the introducing tube 1.

For clarity, the clip units 50 mounted in the introducing tube 1 are named as follows. A clip 81, clip 82, and clip 83 are defined in order from the clip mounted at the most distal end. The clip tightening ring 20 having the clips 81, 82, and 83 engagingly mounted is defined as a clip tightening ring 84, a clip tightening ring 85, and a clip tightening ring 86. The manipulating wire 18 engaged with a respective one of the clips 81, 82, and 83 in the clip tightening ring 20 is defined as a manipulating wire 87, a manipulating wire 88, and a manipulating wire 89.

The manipulating member 19 is inserted into backwardly of the clip tightening ring 86. The manipulating wire 87 is inserted into a gap 91 at the pinch section of the clip 82, and is guided to a clearance 90 between the manipulating member 18 and introducing tube 1 avoiding interference with the clip 83. Then, the manipulating member is inserted into the proximal end portion of the introducing tube 1, as shown in FIG. 23C.

The manipulating wire 88 is inserted into a gap 92 at the pinch section of the clip 83, is guided to a clearance 90 between the manipulating member 19 and introducing tube 1, and is inserted into the proximal end portion of the introducing tube 11. As shown in FIG. 23E, a wire insert hole 95 may be provided at the pinch sections 17c and 17c' of the clips 82 and 83 so that the manipulating wires 87 and 88 can be easily inserted. On the other hand, a manipulating wire 89 is guided to the internal cavity of the manipulating member 19, and is inserted into the proximal end portion of the introducing tube 1.

Three sets of manipulating wires 87, 88, and 89 are thus disposed so as to avoid interference with each other. This makes it easy to insert the manipulating wires 87, 88, and 89 and making it easier to protrude and ligate the clips 81, 82, and 83.

Now, working of a ninth embodiment will be described here.

A distal end of the introducing tube 1 is guided to an object site while the inside of a body cavity is observed by using an endoscope. The clip 81 and clip tightening ring 84 mounted in the introducing tube 1 are protruded from the introducing tube 1. This protrusion is achieved by retracting the introducing tube 1 on the proximal end side. Alternatively, this protrusion is achieved by protruding the manipulating member 19 to the distal end portion side of the introducing tube 1.

Figure 24:
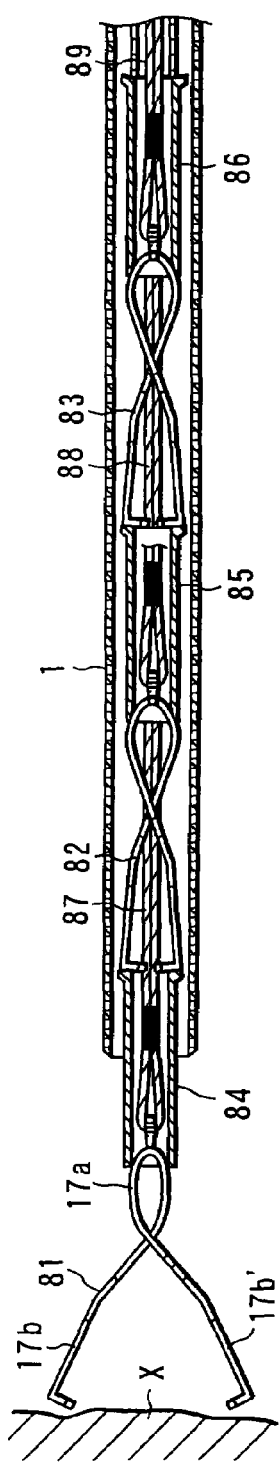
FIG. 24 is a longitudinal side section showing a distal end portion of a apparatus for ligating living tissues for explaining working of the present embodiment.

When the manipulating wire 87 is retracted while the clip 81 and clip tightening ring 84 are protruded from the introducing tube 1, a force applied by the manipulating wire 87 is transmitted to the clip 81. The manipulating member 19 is fixed. Thus, the applied force acts as a compression force between the clip 81 and manipulating member 19. By this compression force, an oval portion of the proximal end portion 17a of the clip 81 is introduced into the clip tightening ring 84. Here, the dimension of the oval portion is larger than the inner diameter of the clip tightening ring 84. Thus, the oval portion is crushed by the clip tightening ring 84, as shown in FIG. 24. Then, the arm sections 17b and 17b' open significantly to the outside.

The compression force acts to the clips 82 and 83 as well as the clip 81. The clips 82 and 83 are not introduced into the clip tightening rings 85 and 86, respectively, and the arm sections 17b and 17b' do not open significantly. That is, the clip 82 and clip tightening ring 85 and the clip 83 and clip tightening ring 86 act as a hard connecting member provided between the clip 81 and manipulating member 19, and receive a compression force applied between the clip 81 and manipulating member 19.

The clips 82 and 83 are not introduced into the clip tightening rings 85 and 86 because the arm sections 17b and 17b' of the clips 82 and 83 are not expanded or opened more than the inner diameter of the introducing tube 1. That is, even if the compression force acts with the clips 82 and 83, expansion/opening of the arm sections 17b and 17b' of the clip 81 stops where the arm sections 17b and 17b' of the clip 81 abut against the internal wall of the introducing tube 1, and no more expansion/opening occurs. Thus, an oval portion does not shrink at the proximal end portion 17a of the clip 81, and is not introduced into the clip tightening ring 20.

While the arm sections 17b and 17b' of the clip 81 open, the clip 81 is guided so as to pinch a target living tissue. By further retracting the manipulating wire 87, the arm sections 17b and 17b' of the clip 81 are introduced into the clip tightening ring 84, and the pinch sections 17c and 17c' of the clip 81 are closed. While the living tissue is reliably pinched between the arm sections 17b and 17b' of the clip 81, the manipulating wire 87 is further retracted, and the hook 17f is extended, thereby releasing engagement between the clip 81 and manipulating wire 87. In this manner, the clip 81 can be retained in the body cavity while the living tissue is pinched.

Then, in order to retain the clip 82 in the living tissue in the body cavity, the manipulating wire 87 separated from the clip 81 is retracted to a location free of interference with the clip tightening ring 86 mounted backwardly. Specifically, the manipulating wire 87 is introduced into the internal cavity of the manipulating member 19. The thus-separated manipulating wire 87 is retracted, thereby making it possible to protrude the clips 82 and 83 more easily. In this state, the introducing tube 1 is retracted to the proximal end side, and the clip 82 is protruded from the distal end of the introducing tube 1.

The subsequent manipulation is completely identical manipulation for retaining the clip 81 at the living tissue. Then, the clip 82 can be retained at the living tissue. By further repeating the same manipulation, a plurality of the clips 81, 82, and 83 mounted in the introducing tube 1 can be retained at the living tissue in the body cavity.

According to the present embodiment, in addition to advantageous effect of the third embodiment, the following advantageous effects are provided. A work of protruding the clips from the introducing tube can be carried out easily and reliably. In addition, the compression force quantity during clip ligation is received between the manipulating member and clip, the force quantity is well transmitted, and ligation can be effected with a small force. In addition, unlike the third embodiment, an engaging member such as blade 8a or 8a' for the clip tightening ring 8 is eliminated, and the manufacturing cost is reduced more remarkably.

Figure 25:
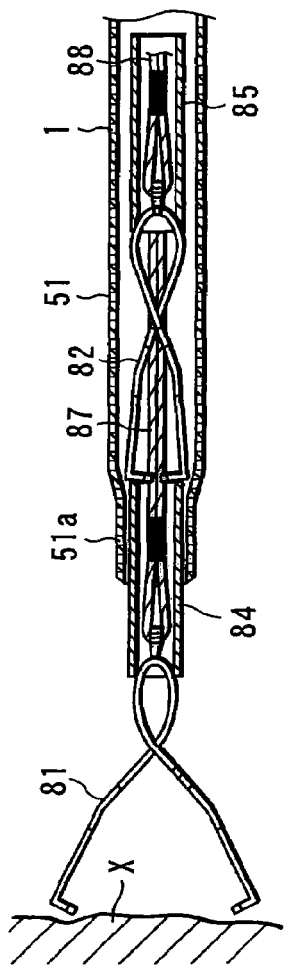
FIG. 25 is a longitudinal side section showing a distal end portion of a apparatus for ligating living tissues for explaining working of the present embodiment.
Figure 26:
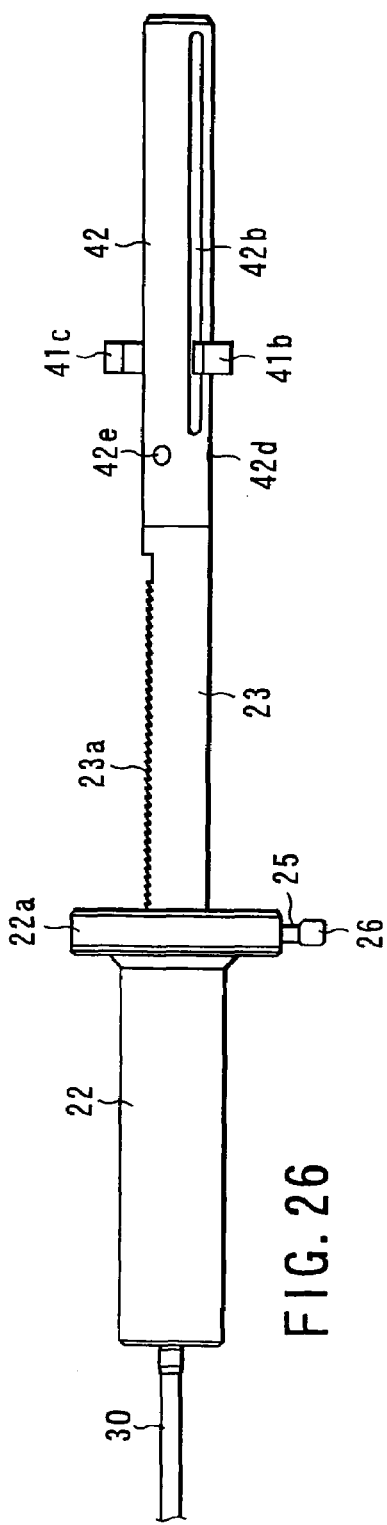
FIG. 26 is a side view showing a manipulating portion with a ratchet for controlling advancement and retraction of an introducing tube according to an eleventh embodiment of the present invention.

FIG. 25 shows a tenth embodiment. Like constituent elements in the ninth embodiment are designated by like reference elements.

The present embodiment is different from the ninth embodiment only in shape of the distal end portion of the introducing tube. An introducing tube 51 according to the present embodiment is reduced in diameter according to the manufacturing method such as thermal molding of the distal end portion 51a of the introducing tube 1 in the ninth embodiment.

The internal diameter at the distal end portion of the introducing tube 1 is formed to be substantially identical to the outer diameter of the clip tightening ring 84. In this manner, at the distal end portion 51a of the introducing tube 51, the clip 81 an clip tightening ring 84 are free from play or being inclined.

The inner diameter of the diameter-reduced portion at the distal end portion of the introducing tube 51 is substantially equal to the outer diameter of the clip tightening ring 84, and is about 1.0 mm to 2.2 mm. In addition, the length of the diameter-reduced portion in an axial direction is such that the clip tightening ring 84 can be fixed, and is 3 mm or longer.

According to the present embodiment, the clip 81 and clip tightening ring 84 extruded by the manipulating member 19 are protruded from the distal end portion 51a of the introducing tube 51. At this time, the clip tightening ring 84 is temporarily fixed to the diameter-reduced portion of the distal end portion 51a of the introducing tube 51, and thus, the clip tightening clip 84 is free from play or being inclined to the introducing tube 51. In this state, the manipulating wire 87 is retracted, thereby enabling the retention of the clip 81 in a living tissue.

Thus, according to the present embodiment, because of the absence of play and inclination of the clip and clip tightening ring, the compression force can be reliably received, and the clips can be retained with smaller force. In addition, the target tissue can be easily aimed at.

FIG. 26 to FIG. 29A to FIG. 29C each show an eleventh embodiment.

As shown in FIG. 27A and FIG. 27B, an introducing tube connecting member 21 is formed in a substantially cylindrical shape, and a cylindrically shaped projection portion 21a is provided at its distal end portion. This protrusion portion 21a is fixed to be press-fit to the proximal end portion of the polymeric resin-based introducing tube 1, and a connecting cylinder body 21c having a mail screw portion 21b at its outer periphery face is provided at the rear end portion.

As shown in FIG. 28A to FIG. 28C, a female screw portion 22a at the distal end portion of the substantially cylindrical shaped introducing tube slider 22 is screwed and connected at the mail screw portion 21b of the introducing tube connecting member 21. A jaw portion 22b is provided at the proximal end portion of this introducing tube slider 22.

The introducing tube slider 22 has a cylindrical internal cavity 22c, and a manipulating member slider 23 is inserted into this internal cavity 22c. The manipulating member slider 23 is formed in a substantially cylindrical shape, and a ratchet 23a is provided along an axial direction partially of its outer periphery face. This ratchet 23a is movably engaged into the internal cavity 22c provided at the introducing tube slider 22. A claw engagement recess portion 22d is provided at the inner periphery portion located at the jaw portion 22b of the introducing tube slider 22, and a claw member 24 is housed in this claw engagement recess portion 22d. The claw member 24 is provided as a substantially rectangular member. At its distal end portion, there is provided a claw 24a that can be engaged with the ratchet 23a of the manipulating member slider 23. A pin 24b is protruded at an intermediate portion at the rear end portion of the claw member 24, and a spring 24c engaged with the pin 24b is provided inside of the claw engagement recess portion 22d. Then, the claw member 24 is biased in the direction of the ratchet 23a by means of a spring 24c. Further, two through holes 22e is punched at the opposite side to the claw member 24 of the jaw portion 22b of the introducing slider 22, and a rod 25 is movably engaged into these three holes 22e. The distal end portion of the rod 25 is fixed to the claw member 24, and a button 26 is provided at its proximal end portion.

When this button 26 is pushed in the direction of the introducing tube slider 22, a force is transmitted to the claw member 24 via the rod 25, and a spring 24c is compressed. In this manner, the claw member 24 is released from engagement with the ratchet 23a provided at the manipulating member slider 23 so that the introducing tube slider 22 can move on the manipulating member slider 23 in an axial direction.

At the inside of the introducing tube 1 connected to the introducing tube connecting member 21, a manipulating member 27 and a proximal end member 28 are connected in an axial direction by means of a connecting member 29. The connecting member 29 is formed in a substantially cylindrical shape, and a cutout portions 29a and 29a' are provided partially of its external surface. Then, the manipulating wires 87 and 88 are guided into the internal cavity of the proximal end member 28 by the cutout portions 29a and 29a'.

The proximal end member 28 is identical to the manipulating member 27 in structure, shape, material, and properties. Dimensionally, the member 28 is formed to be larger than the manipulating member 27 in inner diameter and outer diameter. Of three manipulating wires 87, 88, and 89 guided from the clips 81, 82, and 83 at the distal end portion of the introducing tube 1, the manipulating wire 89 is guided into the internal cavity of the manipulating member 27. This wire passes through the connecting member 29, and is inserted into the internal cavity of the proximal end member 28 intact.

The remaining two wires 87 and 88 are guided to a clearance 90 between the introducing tube 1 and manipulating member 27. These two wires are inserted into a location of the connecting member 29. Then, the wires are guided into the internal cavity of the proximal end member 28 from the cutout portions 29a and 29a' of the connecting member 29 (refer to FIG. 27A). That is, three manipulating wires 87, 88, and 89 guided from the clips 81, 82, and 83 at the distal end portion of the introducing tube 1 are inserted into the internal cavity of the proximal end member 28 via the connecting member 29.

Further, as shown in FIG. 27A, FIG. 27B, and FIG. 28A to FIG. 28C, a cylindrical protection pipe 30 is engaged with the proximal end member 28. In addition, a distal end portion 30a of the protection pipe 30 is welded to a proximal end portion of the proximal end member 28. A proximal end portion 30b of the protection pipe 30 is welded at the distal end portion of the manipulating member slider 23. Three manipulating wires 87, 88, and 89 guided from the internal cavity of the proximal end member 28 are guided to the internal cavity of the protection pipe 30 intact. These wires are inserted into the internal cavity 23b of the manipulating member slider 23. The protection pipe 30 is provided for the purpose of preventing slackness of the manipulating wires 87, 88, and 89 at the internal cavity 22a of the introducing tube slider 22 and easily sliding the manipulating member slider 23.

Manipulating pipes 40a, 40b, and 40c are welded, respectively, at the proximal end portions of the three manipulating wires 87, 88, and 89 guided into the internal cavity of the manipulating member slider 23. Three knobs 41a, 41b, and 41c are welded at the proximal end portions of the manipulating pipes 40a, 40b, and 40c. These three knobs 41a, 41b, and 41c are bonded while the knobs are inclined by 120 degrees in circumferential direction so as to avoid interference with each other. As shown in FIG. 29A to FIG. 29C, a slider seat 42 is fixed at the proximal end portion of the manipulating member slider 23 by means of screws 42d, 42e, and 42f. Three slips 42a, 42b, and 42c are incorporated in the slider seat 42 along the axial direction. Three slits 42a, 42b, and 42c are provided to be inclined in the circumferential direction by 120 degrees. The knobs 41a, 41b, and 41c are engaged respectively with these three slits 42a, 42b, and 42c, and the respective knobs 41a, 41b, and 41c are isolated from each other, making it possible to slide the inside of the slits 42a, 42b, and 42c.

Now, working of an eleventh embodiment will be described here.

The introducing tube 1 is inserted into a body cavity via the forceps channel of the endoscope. At this time, the distal end portion of the introducing tube 1 is located forwardly of the distal end of the clip 81, and the clip 81 is included in the internal cavity.

The introducing tube 1 is inserted into the vicinity of a target tissue, the jaw portion 22b of the introducing tube slider 22 is pinched, and the introducing tube slider 22 is retracted into the proximal end portion. At this time, the endoscope image is well observed, and it is checked that the arm sections 17b and 17b' of the clip 81 are protruded from the distal end of the introducing tube 1. Further, the introducing tube slider 22 is gradually retracted, and the introducing tube 1 is disposed in a location such that the distal end portion of the clip tightening ring 84 is protruded from the introducing tube 1. When the introducing tube slider 22 is retracted, care must be taken so that the arm sections 17b and 17b' of the clip 82 are not protruded from the distal end of the introducing tube 1. If the arm sections 17b and 17b' of the clip 82 are protruded, there is no way to control the clip 81. Thus, this makes it very difficult to clit the clip 81 at a target living tissue.

When the introducing tube slider 22 is retracted, the claw member 24 is always engaged with the ratchet 23a of the manipulating member slider 23 by the biasing force of the spring 24c. Therefore, even if the introducing tube slider 22 is released at one point, the introducing tube slider 22 does not move on the manipulating member slider 23. In addition, the introducing tube slider 22 can move when a force is applied to the traction direction. The claw member 24 and ratchet 23a are engaged with each other so that the slider can not move even if a force is applied in the distal end direction of the introducing tube 1.

When the introducing tube slider 22 is excessively retracted, the engagement between the claw member 24 and ratchet 23a may be released. When the button 26 is pushed into the direction of the jaw portion 22b, the applied force is transmitted to the claw member 24 via the rod 25, and the spring 24c is deformed to be compressed. Then, the engagement between the claw member 24 and ratchet 23a is released.

When the distal end portion of the clip tightening ring 84 is protruded from the introducing tube 1, the knob 41a is retracted. When the knob 41a is retracted, a force is applied to the distal end clip 81 via the manipulating wire 87. Thus, the clip 81 can be retained in the living tissue.

After the clip 81 has been retained in the living tissue, the knob 41a is retracted until the distal end of the manipulating wire 87 is located backwardly of the clip tightening ring 86.

In order to protrude the second clip 82 from the introducing tube 1, the jaw portion 22b of the introducing tube slider 22 is pinched again, and the introducing tube slider 22 is retracted to the proximal end side. Then, the introducing tube slider 22 is retracted up to the position where the distal end portion of the clip tightening ring 85 is protruded from the introducing tube 1. When the distal end portion of the clip tightening ring 85 is protruded from the introducing tube 1, the knob 41b is retracted. When the knob 41b is retracted, a force is applied to the distal end clip 82 via the manipulating wire 88. Thus, the clip 82 can be retained in the living tissue similarly. After the clip 82 has been retained in the living tissue, the knob 41b is retracted until the distal end of the manipulating wire 88 has been located backwardly of the clip tightening ring 86.

By repeating the above manipulation, a plurality of the clips 81, 82, and 83 can be retained in the living tissue.

According to the present embodiment, the introducing tube is retracted, and a work of protruding the clip can be reliably carried out. In addition, a ratchet is provided, thus, a fine protrusion length of the introducing tube can be adjusted.

Figure 30:
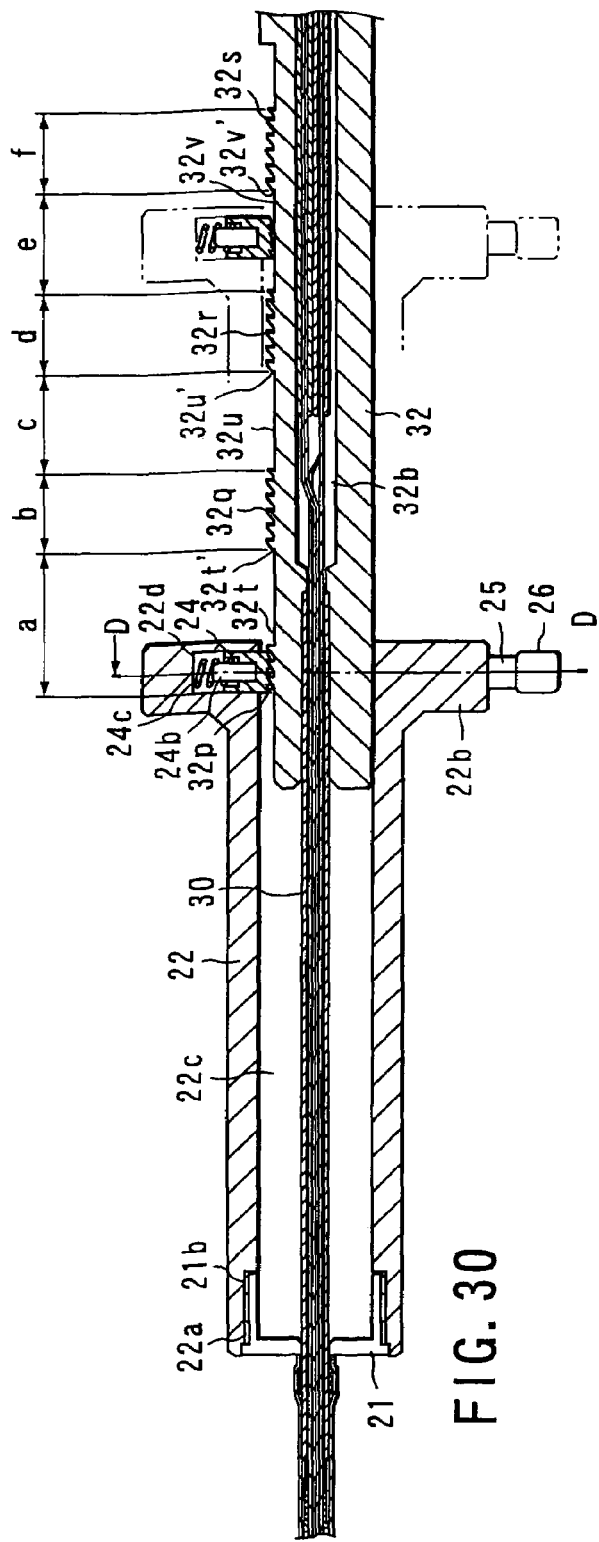
FIG. 30 is a longitudinal side section showing a manipulating portion with a ratchet according to a twelfth embodiment of the present invention.
Figure 31:
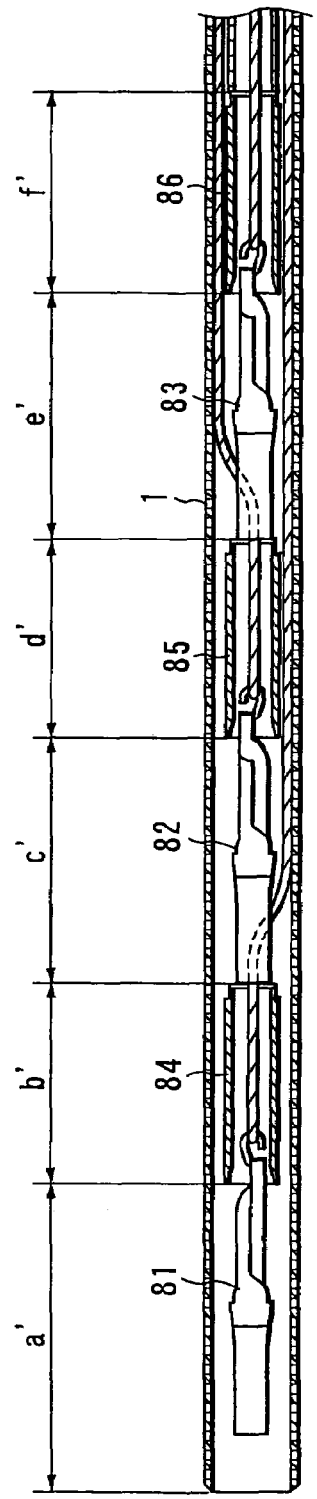
FIG. 31 is a longitudinal side section showing a distal end portion of an introducing tube according to the present embodiment.

FIG. 30 and FIG. 31 each show a twelfth embodiment. The present embodiment is identical to the eleventh embodiment except a ratchet structure of the manipulating member slider 23.

The manipulating member slider 32 is formed by a substantially cylindrical member, and ratchets 32p, 32q, 32r, and 32s are provided along the axial direction over the full outer periphery face, and are engaged into the internal cavity 22c provided at the introducing tube slider 22. When the claw member 24 is not engaged with the ratchets 32p, 32q, 32r, and 32s (when the claw member 24 is located at parallel portions 32t, 32u, and 32v), the inside of the internal cavity 22c of the introducing tube slider 22 can be movably slid without any load.

A length "a'" required for protruding the most distal end clip 81 from the introducing tube 1 corresponds to a length "a" of the manipulating member slider 32 at its frontal manipulation portion side. When the introducing tube 1 is inserted into the channel of the endoscope, the claw member 24 is engaged with the ratchet 32p, and the introducing tube 1 does not slide easily relevant to the mounted clips 81, 82, and 83.

A length b' of the clip tightening ring 84 corresponds to a length of the ratchet 32q. A length c' for protruding the clip 82 from the introducing tube 1 after retaining the clip 81 at the living tissue corresponds to the parallel portion 32u. A length d' of the clip tightening ring 85 corresponds to a length of the ratchet 32r.

A length 'e' for protruding the clip 83 from the introducing tube 1 after retaining the clip 82 at the living tissue corresponds to the parallel portion 32v. A length "f" of the clip tightening ring 85 corresponds to a length of the ratchet 32s.

When the clip 81 is protruded from the introducing tube 1, the claw member 24 abuts against the parallel portion, and thus, the introducing tube slider 22 can be roughly moved. When the clip tightening ring 84 is protruded from the introducing tube 1, the claw member 24 is engaged with the ratchet 32q. Thus, the introducing tube slider 22 can be finely moved. A proper location for protrusion of the clip 81 is a location when the clip tightening ring 84 is at the distal end of the introducing tube 1. Therefore, when the introducing tube 1 is adjusted at this proper location, the introducing tube slider 22 can be finely moved. In addition, the claw member 24 is engaged with the ratchet 32q, whereby the introducing tube slider 22 is heavily manipulated. Thus, a surgeon can recognize that protrusion of the clip 81 is close to the proper location.

Now, working of a twelfth embodiment will be described here.

The introducing tube 1 is inserted into the living body cavity via the forceps channel of the endoscope. At this time, the distal end portion of the introducing tube 1 is located forwardly of the distal end of the clip 81, and the clip 81 is included in the internal cavity. At the manipulating portion side, the claw member 24 is engaged with the ratchet 32p. Thus, the manipulating member slider 32 does not slide the internal cavity 22c of the introducing tube slider 22 easily. Therefore, the clip 81 is not protruded in the forceps channel.

The introducing tube 1 is inserted into the vicinity of a target tissue, and the jaw portion 22b of the introducing tube slider 22 is pinched. Then, the introducing tube slider 22 is retracted to the proximal end side. Then, the claw member 24 rolls over the ratchet 32p at the frontal manipulation portion side, and abuts against the parallel portion 32t. In this manner, the introducing tube slider 22 lightly slides so that the introducing tube slider 22 can be easily retracted. Then, when the introducing tube slider 22 is retracted to the proximal end portion 32t' of the parallel portion 32t, the clip 81 is just protruded from the introducing tube 1 at its distal end side. That is, the introducing tube slider 22 can be roughly moved to a location at which the clip 81 is protruded.

When the introducing tube slider 22 is further retracted, the claw member 24 is engaged with the ratchet 32q, and the sliding resistance of the introducing tube slider 22 increases. In this manner, the surgeon can sensuously recognize that a current location is close to a proper location for protrusion, of the clip 81. Then, the introducing tube slider 22 can be retracted due to the engagement between the claw member 24 and ratchet 32q while the slider is adjusted with a fine length. While the clip tightening ring 84 is protruded from the distal end of the introducing tube 1, the introducing tube 22 is disposed, whereby preparation for ligating the clip 81 completes. In this state, the knob 41a is retracted as in the eleventh embodiment, and the clip 81 is retained at the living tissue.

In order to protrude the clip 82 from the distal end of the introducing tube 1, the introducing tube slider 22 is further retracted, and the claw member 24 is abutted against the parallel portion 32u. The introducing tube slider 22 lightly slides, and the introducing tube slider 22 can be easily retracted again. Then, when the introducing tube slider 22 is retracted to the parallel portion 32u', the clip 82 is just protruded from the introducing tube 1 at the distal end side. That is, the introducing tube slider 22 can be roughly moved to a location at which the clip 82 is protruded.

When the introducing tube slider 22 is further retracted, the claw member 24 is engaged with the ratchet 32r, and the sliding resistance of the introducing tube slider 22 increases. In this manner, the surgeon can sensuously recognize that a current location is close to the normal position for protrusion of the clip 82. Then, due to the engagement between the claw member 24 and ratchet 32r, the introducing tube slider 22 can be retracted while the slider is adjusted with a fine length. While the clip tightening ring 85 is protruded from the distal end of the introducing tube 1, if the introducing tube slider 22 is disposed, preparation for ligating the clip 82 completes. In this state, as in the eleventh embodiment, the knob 41b is retracted, and the clip 82 is retained in the living tissue.

Manipulation for protruding the clip 83 from the distal end of the introducing tube 1 is also achieved by repeating the manipulation. That is, when the introducing tube slider 22 is retracted, and then, the claw member 24 abuts against the proximal end portion 32v' of the parallel portion 32v, the clip 83 is protruded from the introducing tube 1 at its distal end side. That is, the introducing tube slider 22 can be roughly moved to a location at which the clip 83 is protruded.

When the introducing tube 22 is further retracted, the claw member 24 is engaged with the ratchet 32s, and the sliding resistance of the introducing tube slider 22 increases. In this manner, the surgeon can sensuously recognize that a current location is close to the normal location for protruding the clip 83. Then, due to the engagement between the claw member 24 and ratchet 32s, the introducing tube slider 22 can be retracted while the slider is adjusted with a fine length. While the clip tightening ring 86 is protruded from the distal end of the introducing tube 1, the introducing tube slider 22 is disposed, whereby preparation for ligating the clip 83 completes.

In this state, as in the eleventh embodiment, the knob 41c is retracted, and the clip 83 is retained at the living tissue. A plurality of the clips 81, 82, and 83 can be retained at the living tissue due to the manipulation.

In addition, according to the embodiments each, the clip unit is inserted into the body cavity once, whereby a plurality of clips mounted in the introducing tube can be retained in the body cavity. In this manner, a surgical operation time can be reduced, and thus, a patient's pain can be reduced. In addition, manipulating wires are connected to the clips, respectively, and the respective clips can be retained in the body cavity speedily, easily, and reliably.

At the clips, their arm sections and pinch sections open more significantly, and thus, a target tissue to be ligated can be pinched more reliably. In addition, the manipulating wire is disposed so as not to interfere with the clip, thus making it easy to protrude the clip. In addition, the clip can be ligated with smaller force.

A manipulating wire engaged with a clip extends backwardly in straight way, and thus, a loss of force quantity transmission is reduced, whereby making it easy to protrude the clip. The clip can be ligated with smaller force. The manipulating wire is not pinched at the clip pinch portion, thus making it easy to protrude the clip. The clip can be ligated with smaller force. In addition, the arm section of the clip is closed by a clip tightening ring, and thus, a living tissue can be ligated with stronger force.

The manipulating wire is disposed so as not to interfere with means for engaging the clip and clip tightening ring with each other. Thus, the clip can be easily protruded. In addition, the clip can be ligated with smaller force.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus comprising:
   a flexible introducing tube capable of being inserted into a subject and having a distal end, proximal end and a longitudinal axis;
   a plurality of manipulating wires inserted into the introducing tube and being movable along the longitudinal axis in the introducing tube;
   a plurality of clips each of which is connected to the manipulating wire so that the clip is moved towards the proximal end of the introducing tube by moving the manipulating wire towards the proximal end; and
   a flexible pushing member inserted into the introducing tube and being movable toward the distal end of the introducing tube to push one of the clips so that another of the clips is outwardly protruded from the distal end of the introducing tube.

2. The apparatus according to claim 1 wherein said plurality of clips include at least a proximal end side clip and a distal end side clip, and arranged in series along the longitudinal axis in the introducing tube, each of the clips having a proximal end portion and at least two arm sections for pinching a target portion of the subject, the arm sections forwardly extending from the proximal end portion, and being movable between an open position and a close position, and the proximal end portion being connected to the manipulating wire.

3. The apparatus according to claim 2 which further comprises a plurality of tightening rings in the introducing tube, each tightening ring being positioned around the clip to keep the arm sections in the close poison and outwardly protruded from the distal end of the introducing tube together with the distal end side clip.

4. The apparatus according to claim 3 which further comprises an engaging member which is provided at least one of the introducing tube and each of the tightening rings,
   wherein when the distal end side clip which has been protruded from the introducing tube together with the tightening ring is moved toward the distal end of the introducing tube by the manipulating wire, the engaging member engages the introducing tube and the tightening ring, thereby inhibiting the tightening ring from being housed against into the introducing tube.

5. The apparatus according to claim 3 wherein each of tightening ring is extended from the clip toward the proximal end of the introducing tube, the proximal end side clip being pushed by the pushing member through the tightening ring extended therefrom.

6. The apparatus according to claim 5 wherein the tightening ring positioned adjacent clips is contact therewith in the introducing tube.

7. The apparatus according to claim 3 wherein at least one of the proximal end portion of the clip and a distal end of the manipulating wire has a deformed portion which is deformed when the tightening ring are engaged with the introducing tube, so that the proximal end portion of the clip and a distal end of the manipulating wire is disconnected.

8. The apparatus according to claim 2 wherein the pushing member includes a flexible tube for pushing the proximal end side clip.

9. The apparatus according to claim 8 wherein said plurality of manipulating wires are inserted and extended through the flexible tube.

10. The apparatus according to claim 9 wherein the flexible tube includes a plurality of lumens therein extending along the longitudinal axis, each of the manipulating wires being inserted through each of the lumens.

11. The apparatus according to claim 8 wherein the flexible tube includes a compression tube formed by a coiled wire.

* * * * *